US010582894B2

(12) United States Patent
Ben Zrihem et al.

(10) Patent No.: US 10,582,894 B2
(45) Date of Patent: Mar. 10, 2020

(54) REGION OF INTEREST ROTATIONAL ACTIVITY PATTERN DETECTION

(71) Applicant: Biosense Webster (Israel) Ltd., Yokneam (IL)

(72) Inventors: Yaniv Ben Zrihem, Binyamina (IL); Ziyad Zeidan, Zemmer (IL); Roy Urman, Karkur (IL); Stanislav Goldberg, Haifa (IL); Gal Hayam, Tivon (IL); Meir Bar-Tal, Haifa (IL); Atul Verma, Ontario (CA); Yariv Avraham Amos, Tzorit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 254 days.

(21) Appl. No.: 15/404,225

(22) Filed: Jan. 12, 2017

(65) Prior Publication Data

US 2017/0202515 A1    Jul. 20, 2017

Related U.S. Application Data

(60) Provisional application No. 62/278,676, filed on Jan. 14, 2016.

(51) Int. Cl.
*A61B 5/05* (2006.01)
*A61B 5/00* (2006.01)
(Continued)

(52) U.S. Cl.
CPC .......... *A61B 5/6852* (2013.01); *A61B 5/0402* (2013.01); *A61B 5/044* (2013.01);
(Continued)

(58) Field of Classification Search
CPC .... A61B 5/0422; A61B 5/046; A61B 18/1492
See application file for complete search history.

(56) References Cited

U.S. PATENT DOCUMENTS 5,680,860 A   10/1997  Imran
5,938,694 A    8/1999  Jaraczewski et al.
(Continued)

FOREIGN PATENT DOCUMENTS

| CN | 101156774 A | 4/2008 |
| EP | 2 984 986 A2 | 2/2016 |
| WO | 2017/024107 A1 | 2/2017 |

OTHER PUBLICATIONS

Narayan, et al. "Classifying Fractionated Electrograms in Human Atrial Fibrillation Using Monophasic Action Potentials and Activation Mapping: Evidence for Localized Drivers, Rate Acceleration, and Nonlocal Signal Etiologies," Heart Rhythm, Elsevier, US, vol. 8, No. 2, Oct. 11, 2010, pp. 244-253.
(Continued)

*Primary Examiner* — Michael J D Abreu
(74) *Attorney, Agent, or Firm* — Volpe and Koenig, P.C.

(57) ABSTRACT

A method of atrial rotational activity pattern (RAP) source detection is provided which includes detecting, via a plurality of sensors, electro-cardiogram (ECG) signals over time, each ECG signal detected via one of the plurality of sensors and indicating electrical activity of a heart. The method also includes determining, for each of the plurality of ECG signals, one or more local activation times (LATs) each indicating a time of activation of a corresponding ECG signal. The method further includes detecting whether one or more RAP source areas of activation in the heart is indicated based on the detected ECG signals and the one or more local LATs. Mapping information of the detected RAP source areas of activation in the heart is also generated for providing one or more maps.

18 Claims, 16 Drawing Sheets

(51) Int. Cl.
*A61B 5/042* (2006.01)
*A61B 5/046* (2006.01)
*A61B 5/0402* (2006.01)
*A61B 5/044* (2006.01)
*A61B 5/0452* (2006.01)

(52) U.S. Cl.
CPC ............ *A61B 5/046* (2013.01); *A61B 5/0422* (2013.01); *A61B 5/0452* (2013.01); *A61B 5/04525* (2013.01); *A61B 5/6858* (2013.01); *A61B 5/7278* (2013.01)

(56) References Cited

U.S. PATENT DOCUMENTS

| | | | |
|---|---|---|---|
| 6,973,339 | B2 | 12/2005 | Govari |
| 8,433,398 | B2 * | 4/2013 | Zhang ................ A61N 1/3702 600/512 |
| 2002/0022839 | A1 | 2/2002 | Stewart et al. |
| 2002/0055674 | A1 | 5/2002 | Ben-Haim et al. |
| 2003/0093004 | A1 | 5/2003 | Sosa et al. |
| 2004/0059237 | A1 * | 3/2004 | Narayan ............ A61B 5/04525 600/509 |
| 2004/0243012 | A1 | 12/2004 | Ciaccio et al. |
| 2005/0038333 | A1 | 2/2005 | Sra |
| 2007/0197929 | A1 | 8/2007 | Porath et al. |
| 2008/0188765 | A1 | 8/2008 | Stolarski et al. |
| 2009/0112199 | A1 | 4/2009 | Zhang et al. |
| 2009/0253974 | A1 | 10/2009 | Rahme |
| 2011/0054560 | A1 | 3/2011 | Rosenberg et al. |
| 2011/0125041 | A1 * | 5/2011 | Fischell ............ A61B 5/04525 600/515 |
| 2011/0230775 | A1 | 9/2011 | Barley et al. |
| 2011/0251505 | A1 | 10/2011 | Narayan et al. |
| 2013/0006131 | A1 | 1/2013 | Narayan et al. |
| 2013/0116681 | A1 | 5/2013 | Zhang |
| 2013/0131746 | A1 * | 5/2013 | Simon ................ A61N 1/3625 607/9 |
| 2013/0274582 | A1 | 10/2013 | Afonso et al. |
| 2014/0005563 | A1 | 1/2014 | Ramanathan et al. |
| 2014/0052118 | A1 | 2/2014 | Laske et al. |
| 2014/0081114 | A1 | 3/2014 | Shachar et al. |
| 2014/0336520 | A1 | 11/2014 | Zeng et al. |
| 2015/0216435 | A1 | 8/2015 | Bokan et al. |
| 2015/0216438 | A1 * | 8/2015 | Bokan ................ A61B 5/4836 600/515 |
| 2016/0045123 | A1 * | 2/2016 | Bar-Tal ............. A61B 5/04011 600/515 |

OTHER PUBLICATIONS

Allessie et al., "Electropathological substrate of long-standing persistent atrial fibrillation in patients with structural heart disease: Longitudinal Dissociation," Circulation—Arrhythmia and Electrophysiology, pp. 606-615 (Dec. 2010).

De Groot et al., "Electropathological Substrate of Longstanding Persistent Atrial Fibrillation in Patients With Structural Heart Disease: Epicardial Breakthrough," Circulation, pp. 1674-1682 (Oct. 26, 2010).

Houben et al., "S-wave predominance of epicardial electrograms during atrial fibrillation in humans: Indirect evidence for a role of the thin subepicardial layer," Heart Rhythm, vol. 1, No. 6, pp. 639-647 (Dec. 2004).

Inoue et al., "Trigger-based mechanism of the persistence of atrial fibrillation and its impact on the efficacy of catheter ablation," Circulation—Arrhythmia and Electrophysiology, pp. 295-301 (Apr. 2012).

Lee et al., "Simultaneous Bi-Atrial High Density (510-512 Electrodes) Epicardial Mapping of Persistent and Long-Standing Persistent Atrial Fibrillation in Patients: New Insights into the Mechanism of Its Maintenance," Circulation, vol. 132, Issue 22, pp. 2108-2117 (Dec. 1, 2015).

Communication Pursuant to Article 94(3) EPC dated Aug. 28, 2018 for the European Patent Application No. 17151634.7.

Communication Pursuant to Article 94(3) EPC dated Aug. 28, 2018 for the European Patent Application No. 17151625.5.

Extended European Search Report dated May 18, 2017 for the European Patent Application No. 17151625.5.

Extended European Search Report dated May 26, 2017 for the European Patent Application No. 17151629.7.

* cited by examiner

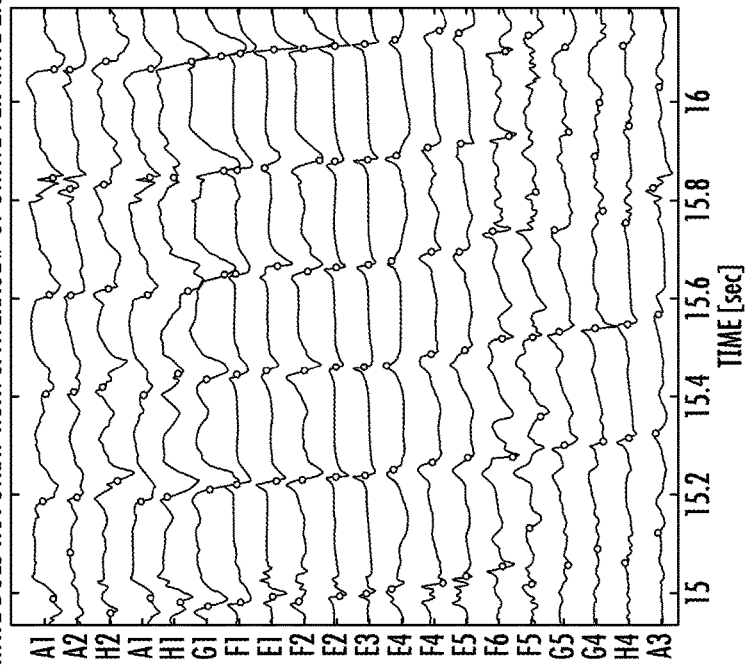
FIG. 10A
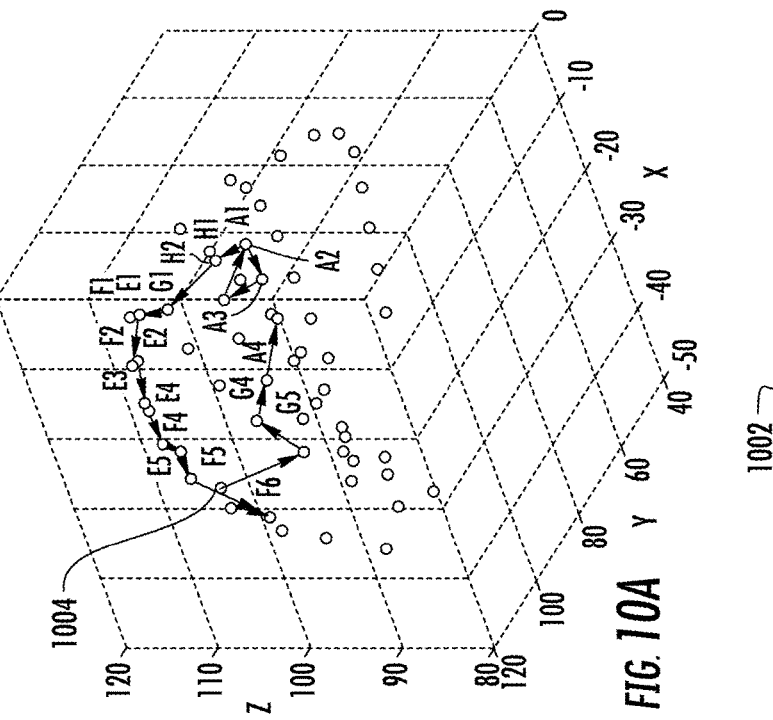
FIG. 10B
| | WAVE ELECTRODES | # OF CYCLES | %CL | START-END OF... | WAVE DURATION | HEAD TO TOE (mm) | HEAD TO TOE (msec) | #SWAVES | %SWAVE | IS SWAVE FIRST? |
|---|---|---|---|---|---|---|---|---|---|---|
| 1 | A1,A2,H2,A1,H1,G1,F1,E1,F2,E2,E3,E4,F4,E5,F6,F5,G5,G4,H4,A3 | 3.5 | 64.25 | 15.185-15.935 | 0.75 | 0.00 | 77.00 | 2.00 | 11.11 | 0 |
| 2 | B1,A1,A2,A3,H3,G3,G2,F1,F2,E1,E2,E3,E4,F5,F6,E7,F8,F7 | 1.57 | 56 | 28.327-28.629 | 0.302 | 52.92 | 84.84 | 1.00 | 6.67 | 0 |
1002
FIG. 10E

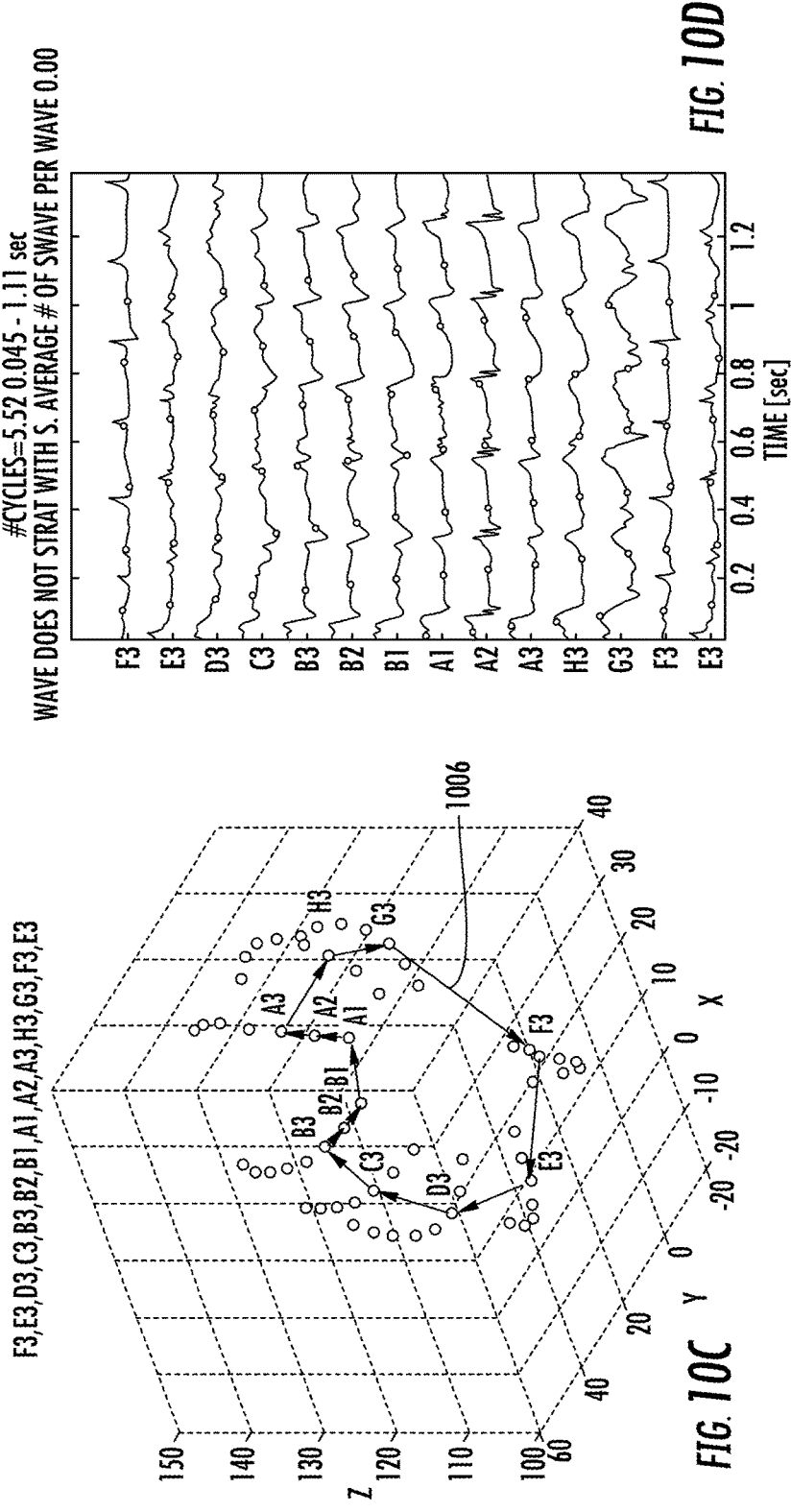

REGION OF INTEREST ROTATIONAL ACTIVITY PATTERN DETECTION

CROSS REFERENCE TO RELATED APPLICATIONS

This application claims the benefit of U.S. Provisional Application No. 62/278,676, filed Jan. 14, 2016, which is incorporated by reference as if fully set forth. This application incorporates by reference as if fully set forth U.S. patent application Ser. No. 15/404,228 titled "Region of Interest Focal Source Detection Using Comparisons of R-S Wave Magnitudes and LATs of RS Complexes," U.S. patent application Ser. No. 15/404,244 titled "Identification of Fractionated Signals," U.S. patent application Ser. No. 15/404,226 titled "Overall System and Method for Detecting Regions of Interest," U.S. patent application Ser. No. 15/404,231 titled "Non-Overlapping Loop-Type or Spline-Type Catheter To Determine Activation Source Direction and Activation Source Type," and U.S. patent application Ser. No. 15/404,266 titled "Region of Interest Focal Source Detection," all filed on Jan. 12, 2017.

FIELD OF INVENTION

The present invention relates to systems and methods for determining regions of interest to be ablated for treatment of cardiac arrhythmia, such as atrial fibrillation, and, more particularly, to systems and methods for detecting atrial fibrillation rotational activity pattern (RAP) sources to determine a region of interest of the heart for ablation.

BACKGROUND

Cardiac arrhythmia includes different types of abnormal or irregular heart rhythms, such as, for example, atrial fibrillation (AF), which is characterized by rapid and irregular beating. Under normal heart conditions, a heartbeat is produced by electrical pulses (i.e., signals) which originate in the upper chambers (i.e., atria) of the heart and pass through the atria through the atrioventricular (AV) node to a pair of lower chambers (i.e., ventricles) of the heart. As the signals pass through the atria, the atria contract and pump blood from the atria into the ventricles. As the signals pass through the AV node to the ventricles, the ventricles are caused to contract, pumping out blood from the heart to the body. During conditions of AF, however, the signals in the atria become chaotic and cause the heart to beat irregularly.

AF can negatively affect the physical, psychological and emotional quality of a person's life. AF can progressively increase in severity and frequency and, if left untreated, may lead to chronic fatigue, congestive heart failure or stroke. One type of AF treatment includes prescribed medications, such as rhythm control medications and medications used to manage the increased risk of stroke. These medications must be taken daily and indefinitely. Another type of AF treatment includes cardioversion, which attempts to restore a normal heart rhythm by providing electric shocks to the heart through electrodes placed on the chest. In some persistent types of AF, cardioversion is either ineffective or cannot be attempted.

Recent approaches for treating AF include minimally invasive ablation procedures (e.g., catheter ablation) in which the heart tissue is ablated to terminate electrical pathways and block faulty electrical impulses that can cause heart rhythm disorders.

SUMMARY

A method of atrial rotational activity pattern (RAP) source detection is provided which includes detecting, via a plurality of sensors, electro-cardiogram (ECG) signals over time, each ECG signal detected via one of the plurality of sensors and indicating electrical activity of a heart. The method also includes determining, for each of the plurality of ECG signals, one or more local activation times (LATs) each indicating a time of activation of a corresponding ECG signal. The method further includes detecting whether one or more RAP source areas of activation in the heart is indicated based on the detected ECG signals and the one or more local LATs.

A system for atrial rotational activity pattern (RAP) source detection is provided which includes a plurality of sensors configured to detect a plurality of electro-cardiogram (ECG) signals each indicating electrical activity of a heart over time. Each of the plurality of sensors is configured to detect one of the ECG signals. The system also includes a processing device comprising one or more processors configured to determine, for each of the plurality of ECG signals, one or more local activation times (LATs) each indicating a time of activation of a corresponding ECG signal and detect whether one or more RAP source areas of activation in the heart is indicated based on the detected ECG signals and the one or more local LATs.

A non-transitory computer readable medium is provided which includes instructions for causing a computer to execute a method of detecting, via a plurality of sensors, electro-cardiogram (ECG) signals over time. Each ECG signal is detected via one of the plurality of sensors and indicates electrical activity of a heart. The instructions further include determining, for each of the plurality of ECG signals, one or more local activation times (LATs) each indicating a time of activation of a corresponding ECG signal and detecting whether one or more RAP source areas of activation in the heart is indicated based on the detected ECG signals and the one or more local LATs.

BRIEF DESCRIPTION OF THE DRAWINGS

A more detailed understanding can be had from the following description, given by way of example in conjunction with the accompanying drawings wherein:

FIGS. 10A and 10B are illustrations of an exemplary RAP;

FIGS. 10C and 10D are illustrations of a simulated exemplary RAP;

FIG. 10E is a table which includes exemplary data used to represent the exemplary RAP source shown in FIG. 10A;

FIG. 10F is a table which includes exemplary data used to represent the exemplary RAP source shown in FIG. 10C;

DETAILED DESCRIPTION

Figure 1:
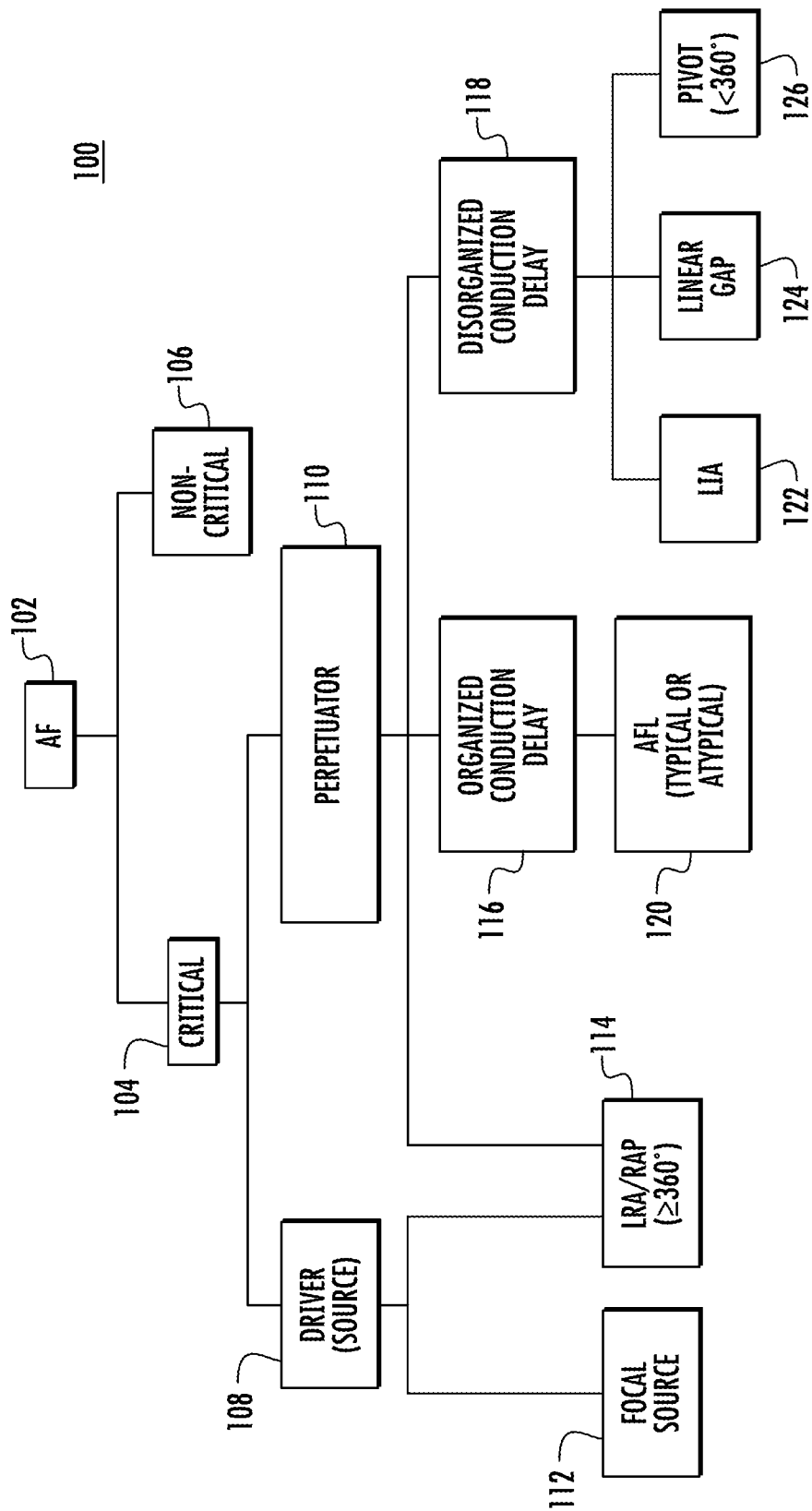
FIG. 1 is a block diagram illustrating an exemplary classification of AF used with embodiments disclosed herein.

Conventional methods and systems used for catheter ablation typically include inserting the catheter through an incision in the skin and guided up to the heart. Before ablation is performed, intra-cardiac electrocardiogram (IC ECG) signals of the heart are acquired via electrodes placed at different areas of the heart. The signals are monitored and used to provide information to determine whether one or more areas of the heart are causing the irregular heart rhythm. The conventional methods and systems used to determine these areas to be ablated, however, are time consuming (e.g., several hours) and rely on medical personnel with specific expertise and experience (typically requiring many hours of training).

Embodiments disclosed herein employ systems, apparatuses and methods for determining potential regions of interest (ROIs) to be targeted for ablation via automatic detection of RAP source areas of activation in the heart. Embodiments disclosed herein are used to potentially reduce map analysis and interpretation training time and increase ablation success rates, such as for ablation aimed at isolation and extinguishing of RAP sources.

Embodiments disclosed herein include implementation of various machine-learning algorithms for detection of RAP sources in real-time. For example, RAP detection may include activation based algorithms such as analyzing activation waves according to spatio-temporal manifestations and identifying centers of sources of activation to determine potential RAP sources. RAP detection algorithms may also include identification of outer circle to inner circle activation spreads using circular type (e.g., Lasso, PentaRay) catheters. In some embodiments, different RAP detection algorithms may each provide RAP score information (e.g., a value) which indicate a likelihood or probability that a potential RAP source is detected using the algorithm. The score information for one or more algorithms may be provided and used to determine a potential ablation ROI.

Embodiments disclosed herein also utilize various mapping techniques, including fast anatomical mapping (FAM) to map the heart cavities for detection of potential RAP sources and provide maps for display, which are used to facilitate efficient and accurate determination of potential ablation ROIs. Mapping techniques utilize various parameters (e.g., cycle, earliness, R-S complex) of ECG signals and detected local activation times (LATs) for generate mapping information indicating potential RAP sources and provide driver maps from the mapping information indicating the potential RAP sources. The driver maps can be combined with perpetuator maps indicating potential perpetuators. The mapping information can also be used to generate maps of the electro-physical conditions of the AF substrate in addition to, or alternative to, maps and video representing a spatio-temporal manifestation of the AF process to facilitate efficient and accurate determination of potential ablation ROIs.

FIG. 1 is a block diagram illustrating an exemplary classification of AF used with embodiments disclosed herein. The exemplary classification in FIG. 1 distinguishes between critical and non-critical AF as well as between drivers and perpetuators of AF and their relative spatio-temporal patterns.

For example, as shown in FIG. 1, an irregular heart rhythm characterized as AF 102 is classified as critical 104 or non-critical 106. Examples of non-critical AF 106 include paroxysmal (i.e., intermittent) irregular heart rhythm episodes in which the heartbeat often normalizes as quickly as within a few seconds or after a few hours, and persistent irregular heart rhythm episodes in which a normal heart may be restored by rhythm medical therapy or a procedure (e.g., cardioversion). Examples of critical AF 104 include long-standing persistent irregular heart rhythm episodes that continue for longer periods of time (e.g., more than a year) in which the heart is in a constant state of AF and the condition is considered permanent.

Critical AF can be classified according to characteristics (e.g., areas of activation) that can be derived from IC ECG signals. Areas of activation may be identified as potential contributing factors to AF. As shown in FIG. 1, critical AF is classified according to different areas of activation, including a potential driver of AF (hereinafter "driver") or potential source of AF (hereinafter "source") 108 and a potential perpetuator 110 of AF (hereinafter "perpetuator"). A driver 108 is an area of activation (e.g., in the atria) where electrical pulses originate to stimulate the heart to contract and which can potentially contribute to AF, for example, by producing fibrillatory conduction to other areas of the atria. A perpetuator 110 is an area of sustained activation (e.g., electrophysiological process/substrate) which can also potentially contribute to AF.

Drivers 108 and perpetuators 110 may be represented (e.g., mapped) according to their spatio-temporal manifestation. As shown in FIG. 1, drivers 108 and perpetuators 110 are classified by exemplary spatio-temporal manifestation types, including focal sources (foci) 112 and localized rotational activation (LRA) sources or rotational activation patterns (RAPs) sources 114. A focal source is a type of driver originating at a small area of the atria which spreads centrifugally from a single point. A RAP 114 source is an irregular region of the heart where the electrical pulses rotate at least 360 degrees about a center area.

FIG. 1 also shows different types of perpetuators 110, including one type which exhibits organized conduction delay 116 and another which exhibits disorganized conduction delay 118. Another type of perpetuator 110 shown in FIG. 1 includes atrial flutter (AFL) 120, characterized by organized conduction delay 116 as well as localized irregular activation (LIA) 122, linear gaps 124 and pivots 126 (i.e., electrical pulses that rotate less than 360 degrees about a center area), characterized by disorganized conduction delay 118. Also, the RAP source 114 is shown as both a driver 108 and a perpetuator 110. Drivers 108 and perpetuators 110 are, for example, separately mapped to facilitate identification of driver types and/or perpetuator types and provide efficient and accurate determination of potential ablation ROIs.

Mapping and identification of drivers 108 and perpetuators 110 can also be based on one or more additional factors which may potentially contribute to AF or parameters which may potentially characterize the AF substrate (i.e., the AF process itself) and/or the manifestation of the AF process. For example, AF parameters or AF factors used to identify potential focal sources 108 include omnidirectional activation spread of activation from a point, earliness (e.g., focal source which starts after an excitable gap), triggers such as fast firing (e.g., short cycle-length and high dominant frequency) foci and breakthroughs (e.g., pulmonary veins (PV), free wall and transmural, endocardial and epicardial) and micro re-entry circuit which manifests as focal source and short-radius re-entry circuits which can manifest as a driver 108 depending on the specific anisotropic structure of the central obstacle.

AF parameters or AF factors used to map and identify RAP sources 114 include, for example, repetitive cycles, rotors which can manifest as a driver source 108, structural or functional anisotropy (e.g., localized or distributed), and short-radius re-entry circuits which can manifest as either a driver 108 or a perpetuator 110, depending on specific anisotropic structure of the central obstacle.

AF parameters or AF factors used to map and identify perpetuators 110 include, for example, extension (increased) path length, anatomical (pathological) block lines, fibrosis, stable functional block lines (e.g., areas of prolonged refractoriness), criticality (e.g., shortest path around block line>path length) and fibrillatory conduction factors (e.g., dissociated waves, re-entry circuit factors).

Figure 2:
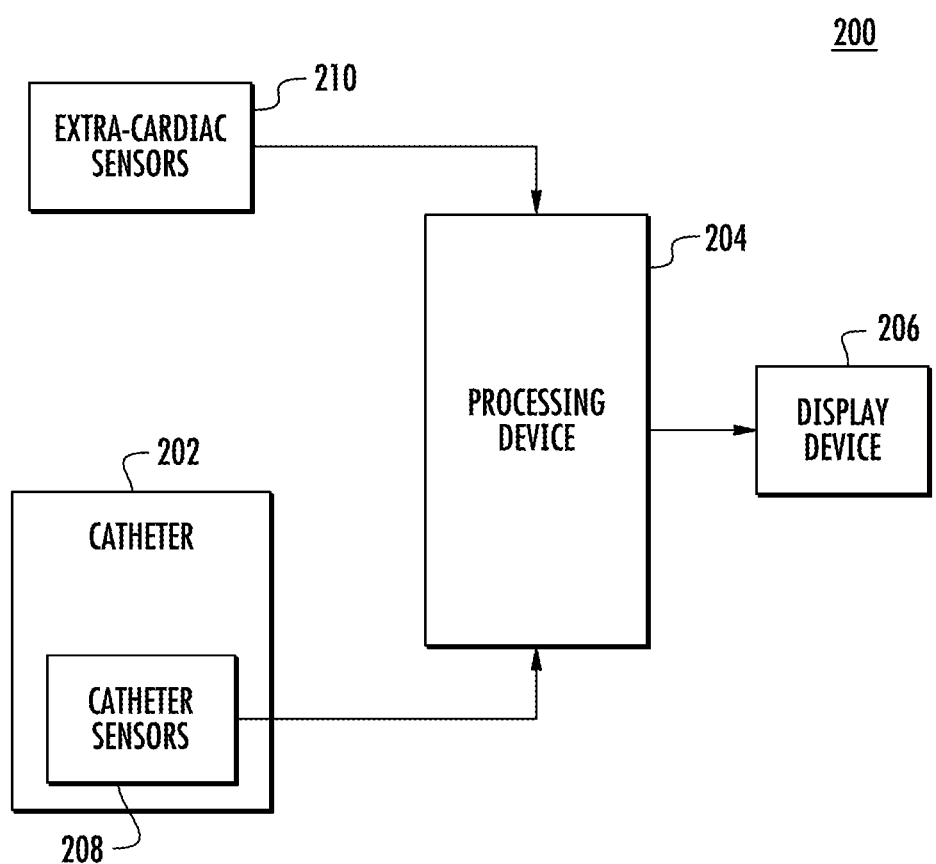
FIG. 2 is a block diagram illustrating an exemplary system which can be used to detect RAP sources for potential ablation ROIs.

FIG. 2 is a block diagram illustrating an exemplary system 200 used to determine AF ROIs for ablation for use with embodiments disclosed herein. As shown in FIG. 2, the system 200 includes a catheter 202, a processing device 204 and a display device 206. Catheter 202 includes an array of catheter sensors (e.g., electrodes) each configured to detect electrical activity (electrical signals) of an area of the heart over time. When an IC ECG is performed, each electrode detects the electrical activity of an area of the heart in contact with the electrode. The system 200 also includes extra-cardiac sensors 210 (e.g., electrodes on the skin of a patient) configured to detect electrical activity of the heart via detection of electrical changes on the skin due to the electro-physiologic pattern of the heart.

The detected IC ECG signals and the detected extra-cardiac signals are processed (e.g., recorded over time, filtered, fractionated, mapped, combined, interpolated, etc.) by processing device 204 and displayed on display device 206.

Embodiments may include any number of sensors 210 used to detect ECG signals, including sensors used to detect IC ECG signals and extra-cardiac ECG signals. For simplification purposes, systems and methods described herein refer to the detection and use of IC ECG signals. It is noted, however, that embodiments may utilize IC ECG signals or extra-cardiac ECG signals or a combination of both IC ECG signals and extra-cardiac ECG signals.

Processing device 204 may include one or more processors each configured to process the ECG signals. Each processor of processing device 204 may be configured to record ECG signals over time, filter ECG signals, fractionate ECG signals into signal components (e.g., slopes, waves, complexes), map ECG signals, combine ECG signal information, map and interpolate mapping information, etc.

Display device 206 may include one or more displays each configured to display ECG signals, ECG signal information, maps of the AF process and maps representing a spatio-temporal manifestation of the AF process.

The catheter sensors 208 and the extra cardiac sensors 210 may be in wired or wireless communication with processing device 204. Display device 206 may also be in wired or wireless communication with processing device 204.

Figure 3A:
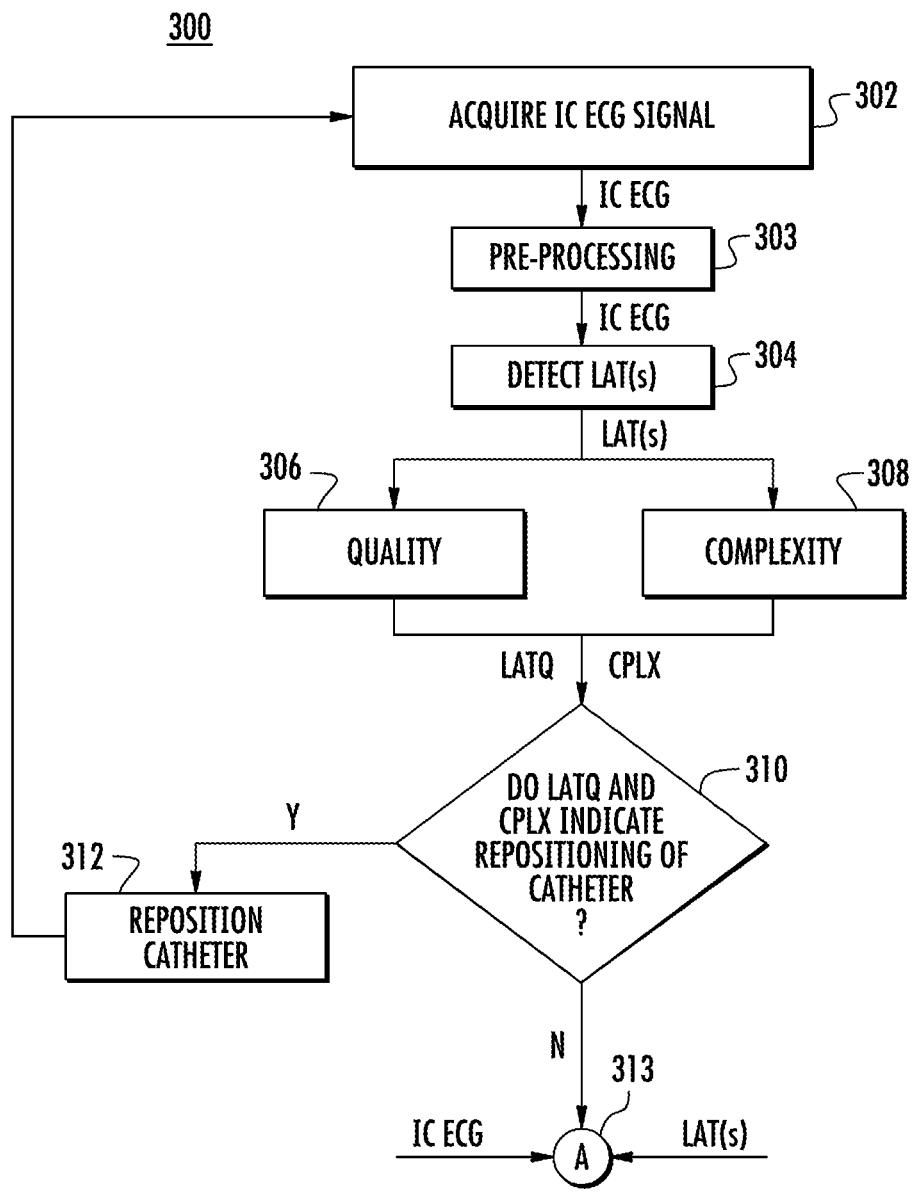
FIGS. 3A and 3B are portions of a flow diagram illustrating an exemplary method which can be used for detection of RAP sources for potential ablation ROIs.
Figure 3B:
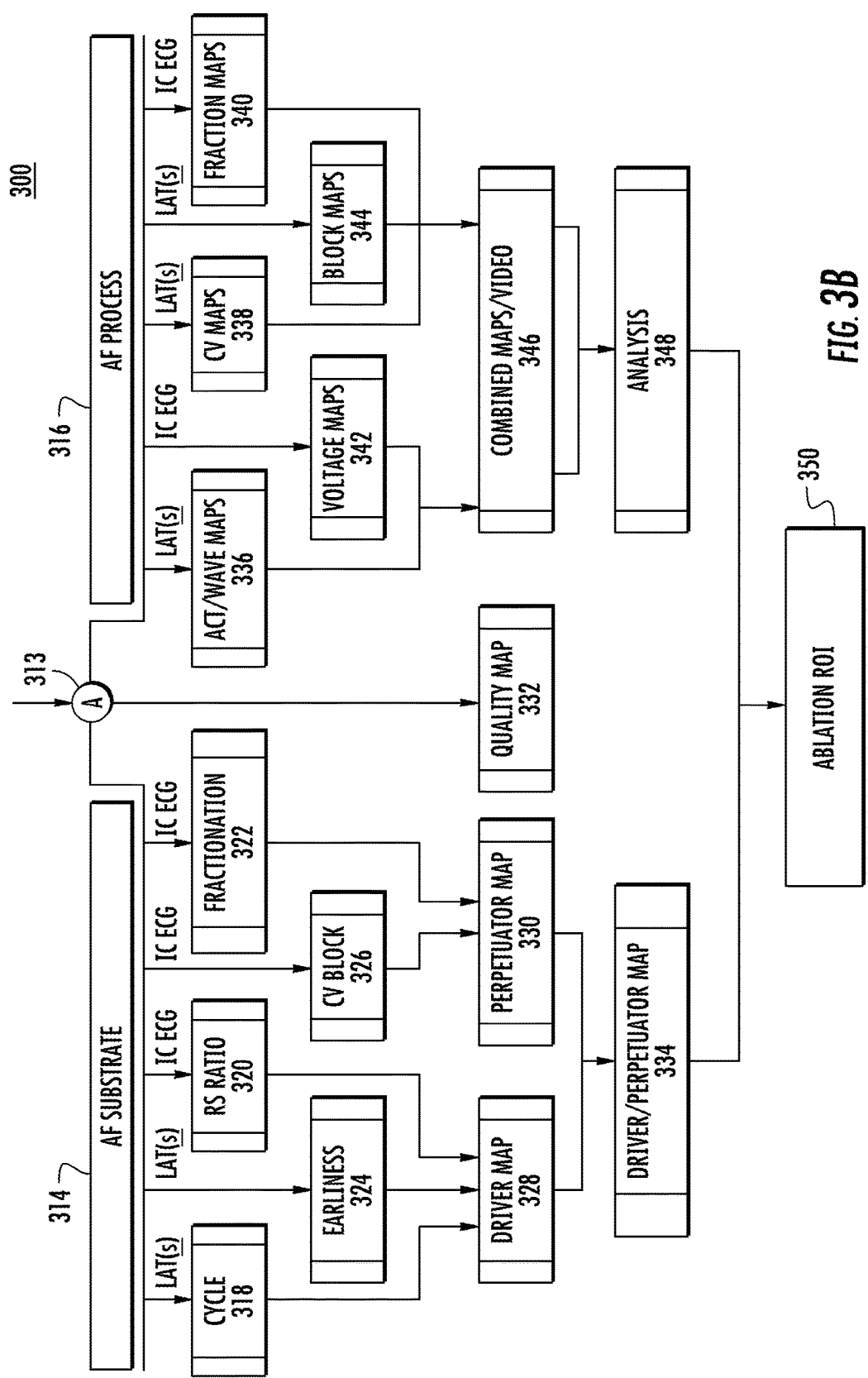

FIGS. 3A and 3B are portions of a flow diagram illustrating an exemplary method 300 of determining a potential ablation ROI. The method 300 employs a mapping taxonomy which includes, from its core moving outward, an IC ECG layer, a pre-processing layer, a LAT detection layer, a map segmentation layer, a map interpolation layer and a map interpretation layer.

FIG. 3A illustrates a portion of exemplary method 300. As shown in block 302 of FIG. 3A, the method 300 includes, as part of the IC ECG layer, acquiring an IC ECG signal which represents electrical activity of an area of the heart. The IC ECG signal acquired at block 302 is, for example, acquired from one of a number of electrodes in contact with different areas of the heart. After acquisition of the IC ECG (302), the method 300 includes, as part of the pre-processing layer, pre-processing of the acquired ECG signal, as shown in block 302 of FIG. 3A, The pre-processing may include execution of one or more algorithms, such as for example, cancellation of ventricular far field signals, baseline correction, and noise reduction. Ventricular far field detection may include, for example, a spatial averaging method (SAM), a temporal averaging method (TAM), a system identification method (SIM) and principal component analysis (PCA).

For each IC ECG signal acquired at block 302, one or more LATs of the corresponding pre-processed IC ECG signal is (are) detected at block 304. The LAT quality (shown as LATQ in FIG. 3A) of each signal is determined at block 306 as part of an exemplary LAT detection layer. The AF complexity (shown as CPLX in FIG. 3A) of the signal is determined at block 308.

As shown at decision point 310, the method 300 includes determining whether to reposition the catheter based on the LAT quality of the signal and the AF complexity. A typical characteristic of high quality IC ECGs is little base line wander (e.g., low baseline vs. IC ECG RMS amplitude, limited ventricular far-field potentials vs. IC ECG RMS amplitude). IC ECG signals characteristics include discernable atrial complexes (e.g., confined (~50 ms) complexes separated by isoelectric segments repeating slopes, 50-200 ms interval; about 150 ms median) during AF. High quality complexes characteristic typically have considerable amplitudes and steep downward slopes (vs. upward slopes) within complexes. Characteristics of the IC ECG signals may be combined into a single measurable characteristic or parameter (e.g., having a measurable value of 0%-100%) to define LAT quality. The LAT quality may be compared to the AF complexity to determine whether to reposition the catheter.

In some embodiments, quality is defined by an ability to map AF for a level of AF complexity. Determining whether to reposition the catheter may include generating a map and determining whether the generated map can be used (e.g., is adequate) to map AF based on whether a level of coverage of a mapping electrode meets (e.g., matches) a level of AF complexity. The ability to map AF for a level of AF complexity may include meeting a map threshold level (e.g., adequate level, trustworthy level). A single parameter (i.e., mapping coverage) is used to define a level of coverage of the mapping electrode. Examples of characteristics that are combined to define the mapping coverage include: (1) contact of the mapping electrode (e.g., contact with active tissue (wall) related to covered area and LAT accuracy); (2)

resolution of the electrodes (e.g., distances and electrode sensitivity radii between electrodes, including mean, minimum and maximum and distances); and (3) quality of the IC ECG and associated annotations provided by a detection algorithm.

AF complexity may include complexity of activation during AF creating wave dissociation (block lines), fusion and wave curvature. Accordingly, a map may be determined as a map which can be used (e.g., trustworthy or adequate) to map AF when, given a certain level of AF complexity (e.g., measured along y-axis), the mapping coverage (including signal and annotation quality measured along x-axis) is sufficient to map the AF complexity. If not, the trustworthiness of the map may become compromised or inadequate.

Signals may then be analyzed using the trustworthy or adequate maps to determine whether the catheter should be repositioned. If it is determined at decision point 310 to reposition the catheter, the catheter (e.g., catheter 202) is repositioned at block 312 and a new IC ECG signal is acquired at block 302. If it is determined at decision point 310 that the catheter should be repositioned, the method 300 continues to "point A" 313 (shown in FIG. 3A and FIG. 3B).

FIG. 3A illustrates the acquiring of a single IC ECG signal for simplification purposes. In practice, however, multiple signals are acquired for each of the plurality of electrodes contacting the heart. Each IC ECG signal acquired at block 202 and the one or more LATs detected for each signal at block 204 are received at "point A" 313.

FIG. 3B illustrates exemplary methods which may be used to determine potential ablation ROIs. As shown FIG. 3B, each acquired IC ECG signal and the one or more detected LATs for each signal are used to generate maps of the AF process that includes the electro-physical conditions of the AF substrate (indicated as the AF Substrate 314 in FIG. 3B) and maps representing a spatio-temporal manifestation of the AF process (indicated as the AF Process 316 in FIG. 3B) as part of an exemplary map segmentation layer.

For example, with regard to the AF Substrate 314 shown in FIG. 3B, the one or more detected LATs are used to independently determine one or more factors or parameters which may contribute to AF. The left side of FIG. 3B illustrates methods which characterize the AF substrate by collecting information over a predefined window of time while assessing a mean interval (e.g., cycle) based on a difference of subsequent LATs 318, first activated (earliness) 324, and morphological aspects of the IC ECG including RS-ratio 320 and fractionation 322 (e.g., fractionated electrograms). For example, the detected LATs are used to independently determine cycle information (e.g., cycle lengths) at block 318 and earliness information (e.g., earliest activation times, early drivers which start after an excitable gap) at block 324. Each IC ECG signal is also used to independently determine R-S complex information (e.g., ratio of R wave to S wave) at block 320 and information obtained by fractionation (e.g., slope information, information indicating an incidence of source behavior presented as the earliest activation from one of a plurality of electrodes, such as showing a percentage that the associated electrode was activated earlier than neighbouring electrodes) of the IC ECG signals at block 322 and CV Block information (e.g., information indicating slowed or blocked conduction (i.e., progression) of electrical impulses through the heart, such as the conduction time (CT) for the electrical pulse to travel a distance in the heart, the path length (i.e., the distance) and the CV of the electrical pulse) at block 326.

As shown, a driver map 328 is generated from the cycle information 318, the earliness information 324 and the R-S complex information 320. A perpetuator map 330 is generated from the CV Block information 326 and the fractionation information 322. As shown, the information used to generate the driver map 328 and the information used to generate the perpetuator map 330 are combined (e.g., a single map, overlaid maps or adjacent maps in one display area) to generate a combined driver/perpetuator map 334. The combined driver/perpetuator map 334 may then be used (e.g., interpolated as part of an exemplary map interpolation layer) to determine one or more ablation ROIs 350.

With regard to the AF Process 316 shown in FIG. 3B, the one or more detected LATs are used to independently generate activation/wave maps 336, CV maps 338 (e.g., maps generated from the CT, the path length and/or the CV of the electrical pulse) and block maps 344 (e.g., maps generated from information indicating a block in the conduction of the signal).

Activation/wave maps may, for example, include a map representing an incidence of source behavior presenting the earliest activation of one of a plurality of electrodes restricted by the same wave, such as indicating a percentage of activation waves detected by a corresponding electrode activated earlier than neighboring electrodes though restricted by neighbors activated by the same wave. Activation Wave maps may, for example, also include a map representing the incidence of electrode positions associated with a fibrillation wave start.

Each IC ECG signal is used to independently generate voltage maps 342 and fraction maps 340. The information used to generate maps 336-344 is combined to provide combined maps or video 346. In some embodiments, the information used to generate the activation/wave maps 336 and Voltage maps 342 is combined to generate a combined activation/wave/voltage map or video and the information used to generate the CV maps 338, the block maps 344 and the fraction maps 340 are combined to generate a combined CV/block/fraction map or video. The combined maps/video 346 are analyzed (e.g., interpreted by medical personnel as part of an exemplary map interpretation layer) at block 348 to determine ROIs to be ablated at block 350. The combined maps/video 346 represent a spatio-temporal manifestation of the AF process which can be easily visualized and interpreted, facilitating an efficient and accurate process for determination of ROIs for ablation. Determined ROIs may be represented (e.g., displayed), for example, by color, by 3-D contour on a 4-D map, by icons (e.g., dynamically changing icons), etc.

In some embodiments, both the combined driver/perpetuator map 334 and the combined maps/video 346 are used to determine ROIs for ablation at block 350. In some embodiments either the combined driver/perpetuator map 334 or the combined maps/video 346 are used to determine ROIs for ablation at block 350. For example, the combined driver/perpetuator map 334 can be used to determine ROIs for ablation at block 350 without using (e.g., viewing, analyzing) the combined maps/video 346.

In some embodiments, the quality map 332 is also used in combination with the combined driver/perpetuator map 334 and/or the combined maps/video 346 to determine ROIs for ablation at block 350. The quality map 332 is used, for example, to facilitate determination of a confidence level or trustworthiness level of the generated maps (e.g., driver map 328, perpetuator map 330 and driver/perpetuator map 334) related to AF substrate 314 and the generated maps (e.g., activation/wave maps 336, CV maps 338, fraction maps 340, voltage maps 342 and block maps 344) related to the AF process 316 parameters. If the quality of the quality map is low, the generated maps are less trusted and appointing an ablation ROI (350) must be regarded with an increase level of care (e.g., by a physician) compared to when the quality map indicates high quality signals (IC ECGs) as the basis for the generated maps.

In some embodiments, determining ROIs for ablation at block 350 includes appointing or selecting one or more ablation sites for use in determining one or more ROIs for ablation. For example, ablation sites may be appointed or selected from driver evidence and perpetuator evidence (e.g., determined from the driver map 328, the perpetuator map 330 or the combined driver/perpetuator map 334) and ROIs may be determined based on the appointed sites.

The maps and mapping techniques disclosed herein potentially: (i) reduce AF map analysis training time; (ii) reduce time to determine ROIs for ablation; (iii) facilitate efficient interpretation of AF maps; and (iv) increase ablation success rates for ablation aimed at isolation and extinguishing of drivers, path lengthening, slowing of re-entry circuits, fibrillatory conduction and fractionated potentials.

Figure 4A:
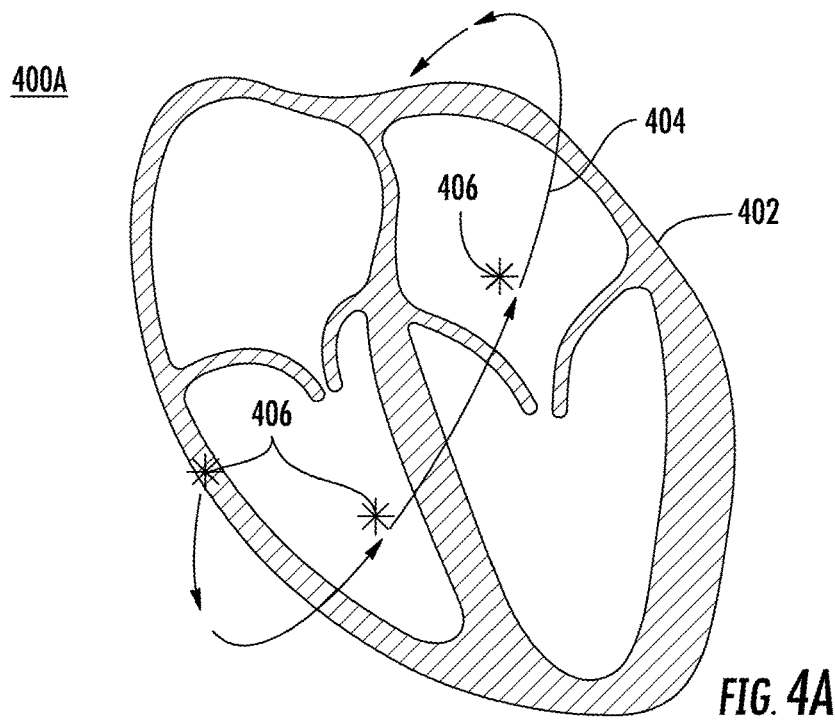
FIGS. 4A and 4B are diagrams of hearts illustrating exemplary RAPs at different heart locations.
Figure 4B:
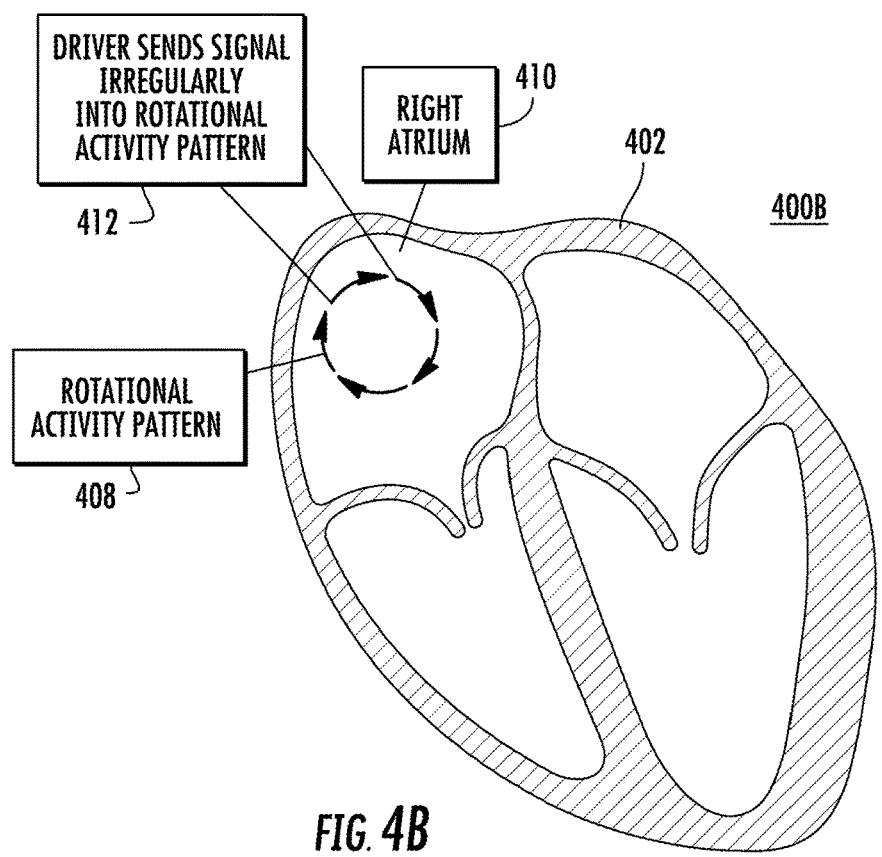

As described above, embodiments disclosed herein employ systems, apparatuses and methods for determining potential ROIs to be targeted for ablation via automatic detection of RAP source areas of activation in the heart. FIGS. 4A and 4B are diagrams 400 of a heart 402 illustrating exemplary RAPs 404 and 408 at different heart locations. For example, diagram 400A at FIG. 4A illustrates a RAP 404 rotating around heart 402. A driver can send a signal irregularly into RAP at different locations 406 of the heart 402. Diagram 400B at FIG. 4B illustrates a RAP 408 rotating circularly at an area of the right atrium 410 of heart 402. The driver sends the signal irregularly into the RAP 408 at locations 412 of the heart 402. The size, shape and locations of the RAPS 404 and 408 as well as locations 406 and 412 in FIGS. 4A and 4B are merely exemplary. A RAP event may be defined by a minimum number of turns or rotations. Intensity of a RAP may be defined by a value based on the number of turns.

RAP detection may include: activation based algorithms which follow activation waves according to a spatio-temporal analysis; identification of outer circle to inner circle activation spreads using circular type (e.g., Lasso, PentaRay) catheters; and identification of stable morphologies (e.g., cycle length (CL) and morphology).

Activation Based Algorithms

Figure 5:
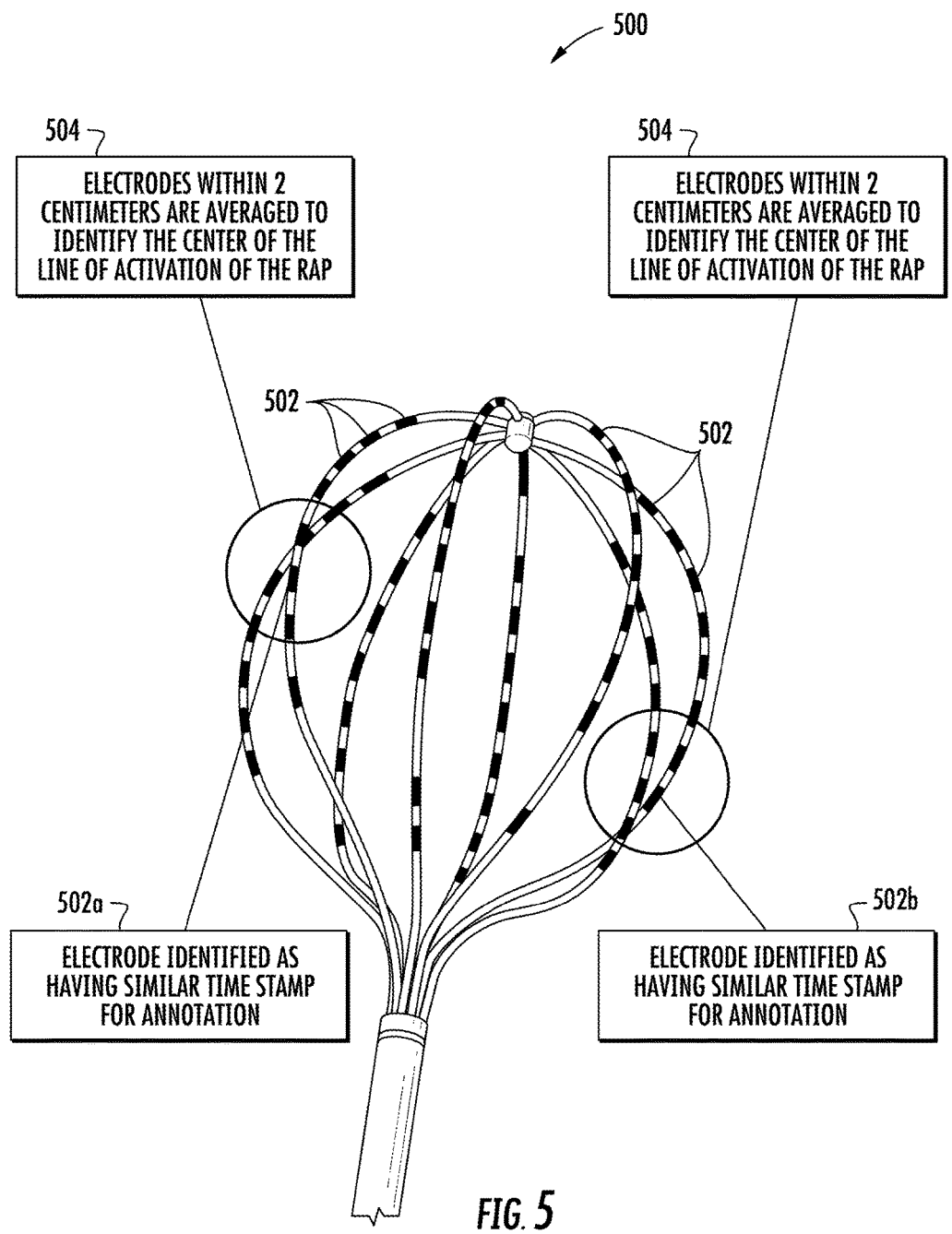
FIG. 5 shows an exemplary basket type catheter which may be used to detect a RAP according to an embodiment.

FIG. 5 shows an exemplary basket type catheter 500 which may be used to detect RAPs according to an embodiment. For example, as shown in FIG. 5, the basket catheter 500 includes a plurality of electrodes 502. ECG signals, indicating electrical activity of a patient's heart and corresponding to each electrode 502 may be detected. Medical personnel (e.g., physician) may identify electrodes 502a and 502b as having similar time stamps for annotation. The physician may identify any number of electrodes 502 having similar annotations. After identifying electrodes 502a and 502b, other neighboring electrodes within a predetermined range (e.g., 2 centimeters of those having similar annotation) are identified. An exemplary range is indicated by circles 504 in FIG. 5. Parameters of the neighboring electrodes may be calculated (e.g., averaged) to identify a center of a line of activation of an RAP.

Figure 6:
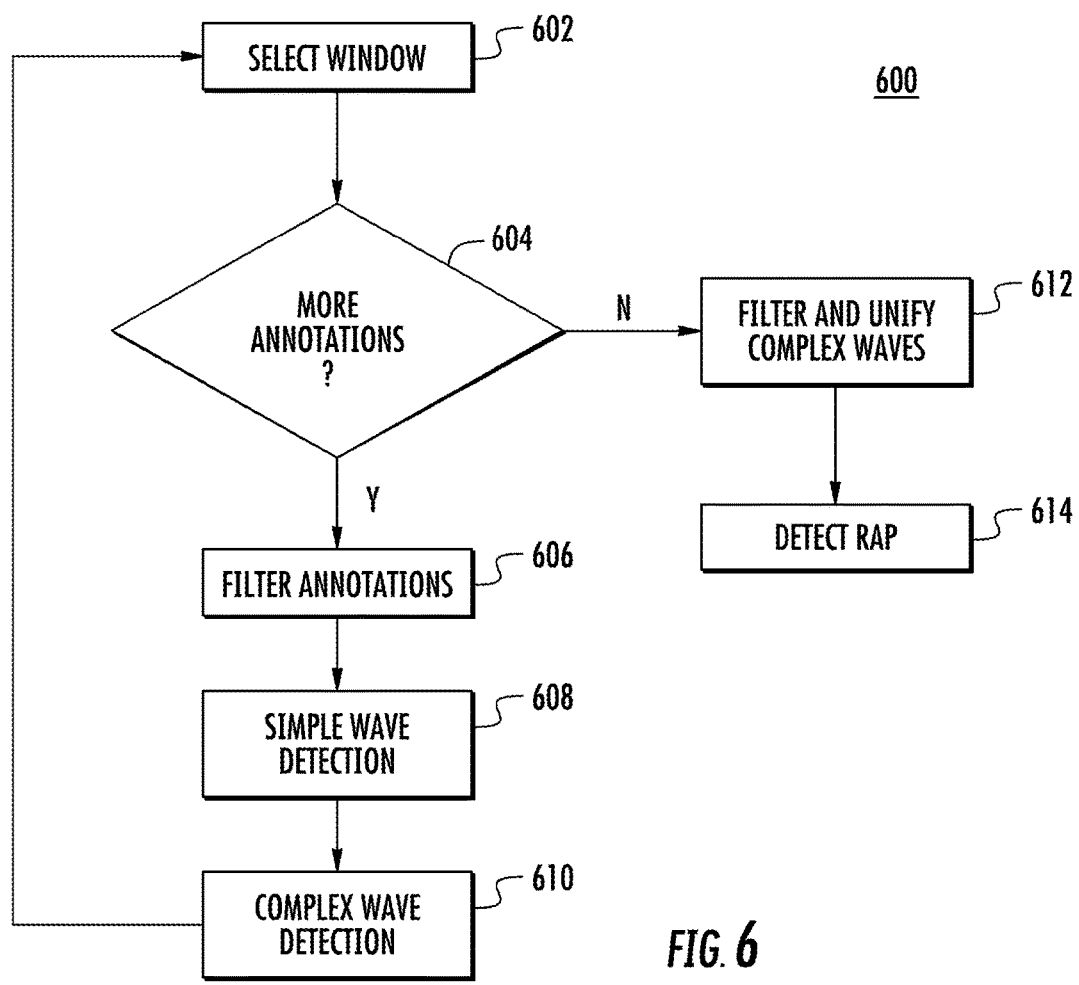
FIG. 6 is a flow diagram illustrating an exemplary method of RAP source detection according to an embodiment.

FIG. 6 is a flow diagram illustrating an exemplary method 600 of RAP source detection according to an embodiment. For explanation purposes, the method 600 shown in FIG. 6 is implemented using an example analysis of recordings of acquired IC ECG signals via a 64-electrode basket catheter. The method may, however, be implemented using different types of catheters and using a different number of electrodes. In this example, the recordings are used to generate a ROI which can be visually identified as a RAP source potentially associated with rotors and which can be targeted for ablation (e.g., radiofrequency ablation (RFA)).

In this example, unipolar electrogram (EGM) activation data is presented in real-time and the EGM data is filtered for quality and far-field ventricular EGM. The unipolar EGMs are automatically annotated. Dominant frequency (DF) analysis and automated EGM analysis is performed to identify QS patterns and "regular" activation gradients occupying >50% of the cycle length suggestive of wavefronts emanating from a single source. Atrial automatic annotations are the raw data for RAP detection. Simple propagation of atrial conduction wave is investigated based on single electrode.

As shown at block 602 in FIG. 6, the method 600 includes selecting a window of time for atrial annotations. Simple waves are iteratively determined for each electrode in a given window. For each electrode currently being investigated in a window of time, a "simple wave" of conduction is defined by the most probable electrode from which the wave is propagating toward the electrode being investigated and according to the most probable electrode to which the wave is propagating from the electrode being investigated. The most probable electrodes are neighboring electrodes having the closest activation with valid conduction velocities (above 0.1 and below 15 mm/sec).

Figure 7:
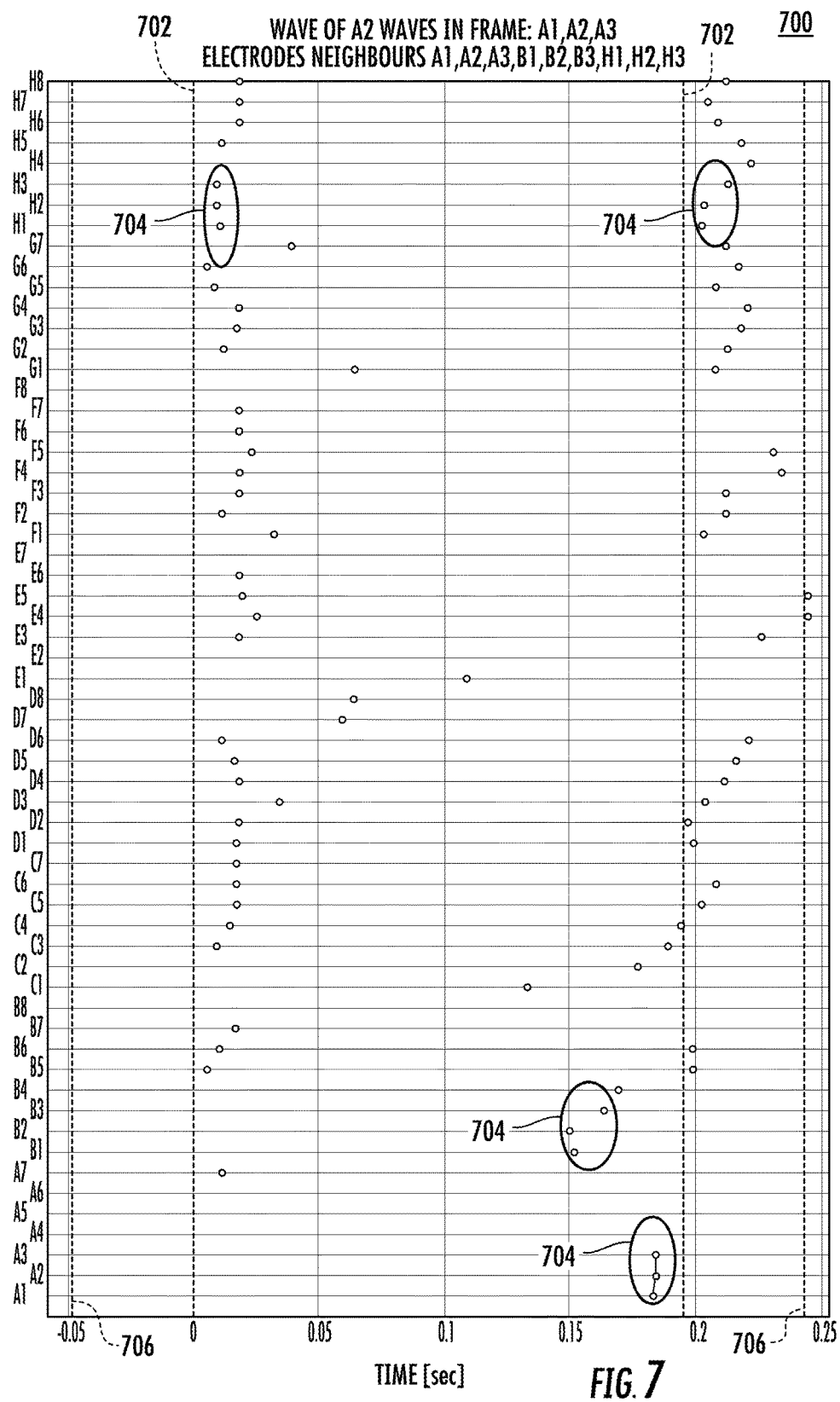
FIG. 7 is a graphical example of the formation of a wave for an electrode according to the method shown in FIG. 6.

FIG. 7 is a graphical example of determining the formation of a wave for electrode A2. As shown in FIG. 7, a plurality of electrodes (A1, A2, . . . H8) are shown on the Y-axis and the time (in seconds (s)) is shown on the X-axis. A window of time is selected between the dashed lines 702 from time 0.0 s to time 0.19 s. The window corresponds to an average cycle length. The dots shown in FIG. 7 represent the atrial annotations for corresponding electrodes. Dots 704 represent the atrial annotations that are valid to form a wave for electrode A2. The remaining dots are ignored because they are spatially distant from A2.

The window may for example, include a window which illustrates a cycle length of a signal±a percentage (e.g., 20%) of the cycle length. For example, as shown in FIG. 7, the window has an additional 20% margin which is defined by the dashed lines 706. The additional margin is used to find the most probable electrodes that are not in the window of interest, which increases the potential coverage of a complex wave behind the current cycle length.

A determination is made, at decision block 604, as to whether any additional annotations (e.g., electrodes having similar time stamps) are to be made. For example, as described above, simple waves are iteratively determined for each electrode in a given window using the annotations the electrodes. Accordingly, after Electrode A2 is investigated, a simple wave is determined for another electrode (e.g., Electrode A3) using the atrial annotations that are valid to form a wave for electrode A3.

Referring back to FIG. 6, if it is determined that there are additional annotations (i.e., the iterations are completed for each of the electrodes), the annotations are filtered at block 606. For example, for each atrial annotation (corresponding to an electrode) investigated, the atrial annotations in the vicinity of the investigated electrode having a cycle length below a cycle length threshold are filtered from the analysis. Automated EGM analysis is performed to identify QS patterns and "regular" activation gradients occupying >50% of the cycle length suggestive of wavefronts emanating from a single source.

Simple wave detection may then be performed at block 608. For example, as shown in FIG. 7, Electrode A1 and Electrode A3 are the "most probable" electrodes in the wave because they have the closest activation with valid conduction velocity. Accordingly a simple wave may be formed by A1→A2→A3.

Figure 8A:
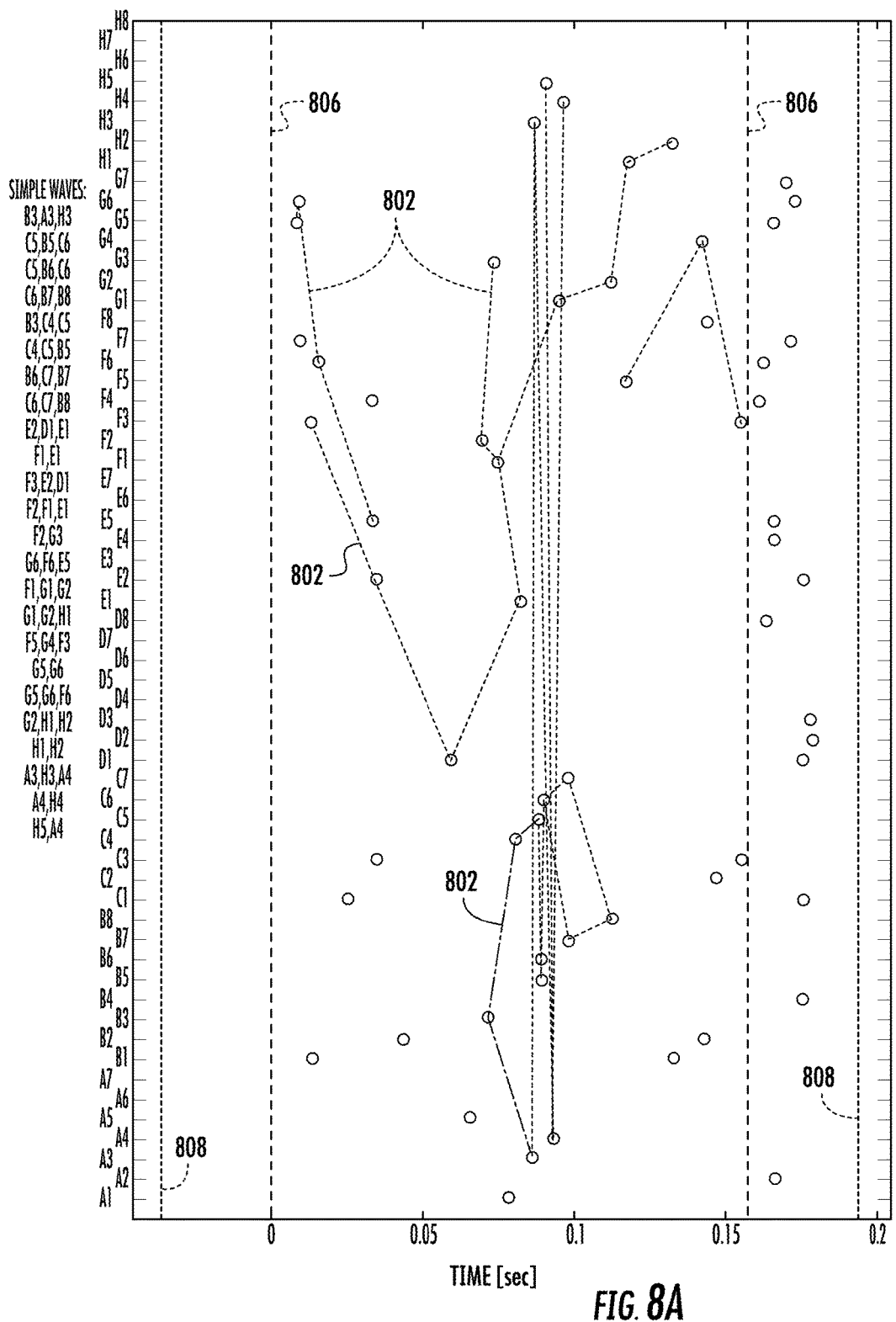
FIGS. 8A and 8B are diagrams illustrating the construction exemplary simple waves and exemplary complex waves.

FIG. 8A illustrates the construction of a plurality of exemplary simple waves 802. As shown in FIG. 8A, simple waves 802 may be iteratively constructed from each one of the annotations in a window (as defined by dashed lines 806 in FIG. 8A). The electrodes used to form the simple waves 802 are shown on the left side of FIG. 8A. The starting point and ending point of the window may then be increased by a predetermined amount (e.g., CL/2) and simple waves are detected in the new window (as defined by dashed lines 808 in FIG. 8A).

After the simple waves 802 are formed, complex wave detection is performed at block 610. For example, using the current example, a complex wave can be formed from a set of up to 64 simple waves. One or more main waves can be constructed and simple waves are added which overlap with the main wave from its beginning and from the end.

Figure 8B:
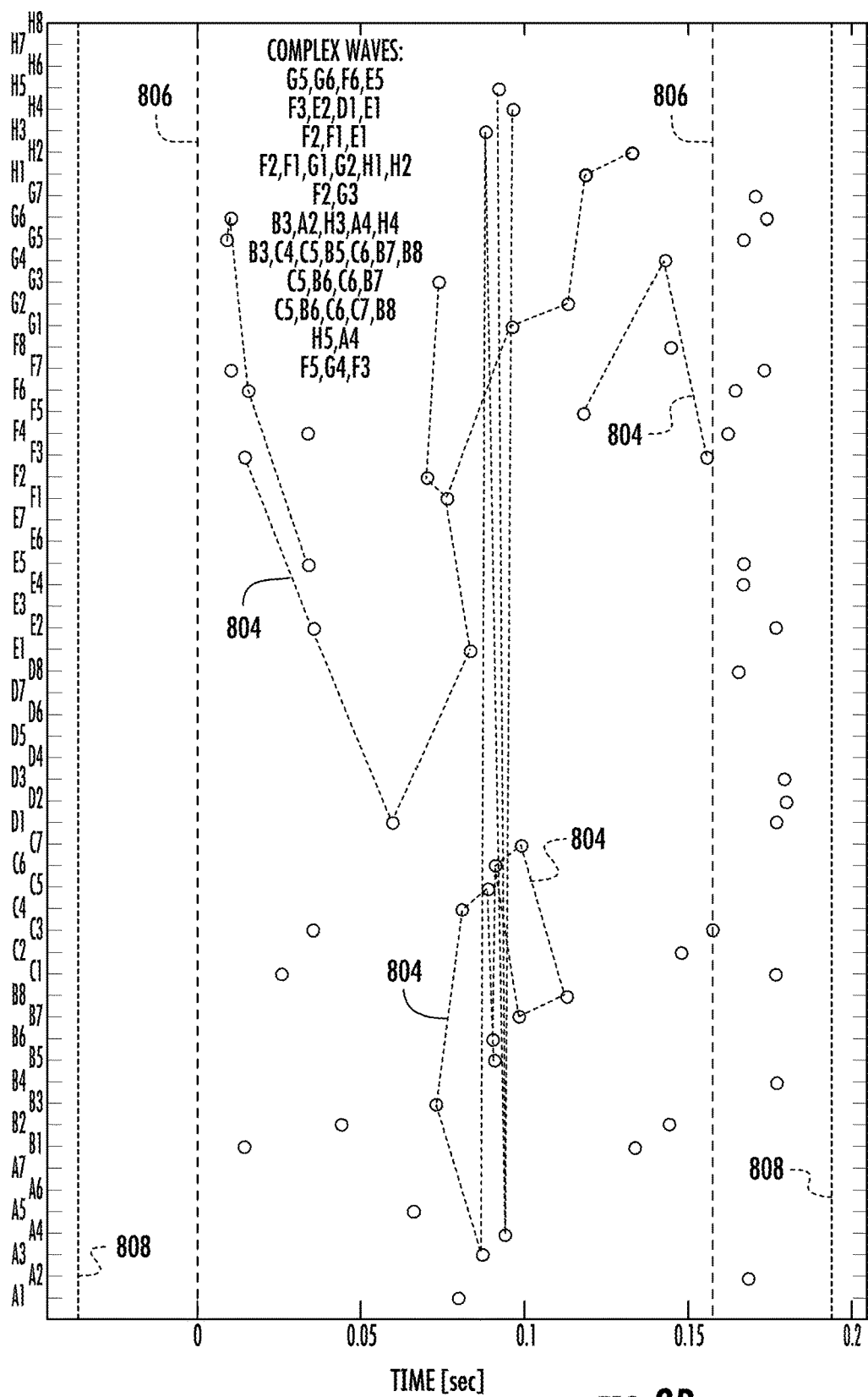

FIG. 8B illustrates the construction of a plurality of exemplary complex waves 804 in the window (as defined by dashed lines 806 in FIG. 8B formed from simple waves 802. For example, complex wave (G5→G6→F6→E5) is assembled from simple waves (G5→G6→F6), (G5→G6) and (G6→F6→E5). The simple wave (G5→G6) is the wave constructed for Electrode G5. Because no atrial activity is determined before G5, G5 is the starting point of the complex wave. Further, because Electrode E5 is an isolated point, no atrial activity is determined after this point and the complex wave is terminated at electrode E5.

An example is now described to explain the forming of a complex wave based on the following simple waves (B5→B6→A7; A7→B7→C6; C6→C7; H3→H4; H1→H2→H3). A complex wave is initialized with the first simple wave (B5→B6→A7). Because the end of the main wave (A7→B7→C6) and the beginning of the simple wave (A7, B7, C6) overlaps at electrode A7, the two waves are added to construct a complex wave (B5→B6→A7→B7→C6). Because the third simple wave (C6→C7) overlaps with the end of the main wave at electrode C6 the two waves are added to construct the complex wave (B5→B6→A7→B7→C6→C7).

Because the next two simple waves (H3→H4 and H1→H2→H3) do not overlap with the complex wave (B5→B6→A7→B7→C6→C7), they are not added to form a larger complex wave. The next two simple waves (H3→H4 and H1→H2→H3) are used to form the next complex wave (H1→H2→H3→H4). For each complex wave, a set of parameters (e.g., duration, existence of S-waves, and the percentage of the wave to the cycle length (hereinafter "% CL")) is calculated. If % CL is lower than a threshold % CL (e.g., 50%), the wave is ignored from further analysis.

If two electrodes from a simple wave intersect with a complex wave (i.e., not in the boundary of the wave), the main wave is split into two waves (e.g. combining complex wave B5→B6→A7→B7 with simple wave B6→A7→A8 to form two complex waves (B5→B6→A7→B7 and B5→B6→A7→A8).

After the complex waves are formed for a given window, the starting point and ending point of the window is increased by a predetermined amount (e.g., CL/2) and complex waves are detected in the new increased window (as defined by dashed lines 808 in FIG. 8B). After complex wave detection is completed at block 610, the method proceeds back to block 602. The process is iterated until each of the annotations (for each electrode) is analyzed.

If it is determined that there are no additional atrial annotations, the complex waves are filtered and unified at block 612. That is, when the process is completed, each of the "one cycle" complex waves is integrated to form a RAP. The complex waves that occupy less than 50% from cycle length are filtered. Because the basic window for analysis is based on CL and two consecutive windows overlap by CL/2, the same complex wave may be detected more than once. Therefore, the same complex waves are filtered from further analysis. For example, two complex waves are considered the same when: (1) more than 90% overlap in duration exists between the waves; and (2) more than 75% of the atrial annotations forming the waves are identical. In this case, the shorter wave is filtered.

When each of the complex waves are filtered and unified, the potential RAP is detected at block 614.

RAPs are constructed from: (1) two or more consecutive pansystolic waves which span more than 50% of the CL; and (2) two or more cycles are within a threshold cycle range. A RAP can, however, move between cycles. Therefore, each transition of the waves between electrodes is counted to represent a static view of the RAP and to extract the distance (e.g., in millimeters) between the starting point of the RAP to the end point of the RAP. The conduction path from electrode to a neighbor electrode is determined by the maximum transition from the electrode to its neighbor. For example, if electrode A2 is participating in a RAP with 5 cycles, three wave propagate from A2 to B2, a fourth wave propagates from A2 to A1 and electrode A2 is missing from the fifth wave, then the RAP is considered to propagate from A2 to B2 for the static representation. When each conduction path is formed, a static representation of the wave is obtained and the Euclidian distance between the two taps of the wave defines the distance between the head and the toe of the wave.

Potentially, the general property of atrial activation seen by a given electrode remains similar during two or more cycles of RAP. In some embodiments, consecutive waves (up to 300 msec difference between their starting points) are considered RAP events if a percentage of identical transitions between electrodes in the wave are equal to or greater than a predetermined transition threshold (e.g., 35%).

In some embodiments, a similarity between two atrial activations may be implemented using the cosine similarity index:

$$\text{similarity} = \frac{\text{wave } a \cdot \text{wave } b}{\|\text{wave } a\| \cdot \|\text{wave } b\|} \quad \text{Equation 1}$$

where • is the dot product of the two waves and ‖wave x‖ is the norm of the wave. A RAP is valid if a percentage of the electrodes is equal to or greater than a predetermined similarity threshold (e.g., 50%), thereby exhibiting an isomorphic property (i.e. the cosine similarity index is above 0.5).

Figure 9A:
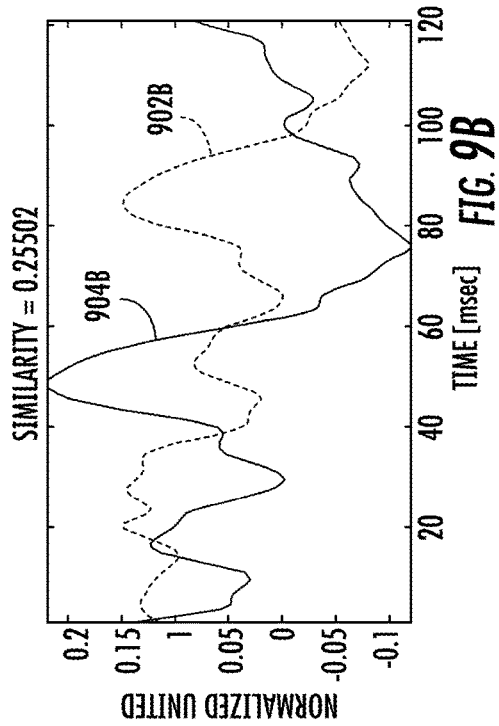
FIGS. 9A through 9D are diagrams illustrating examples of waves having different degrees of similarity.
Figure 9B:
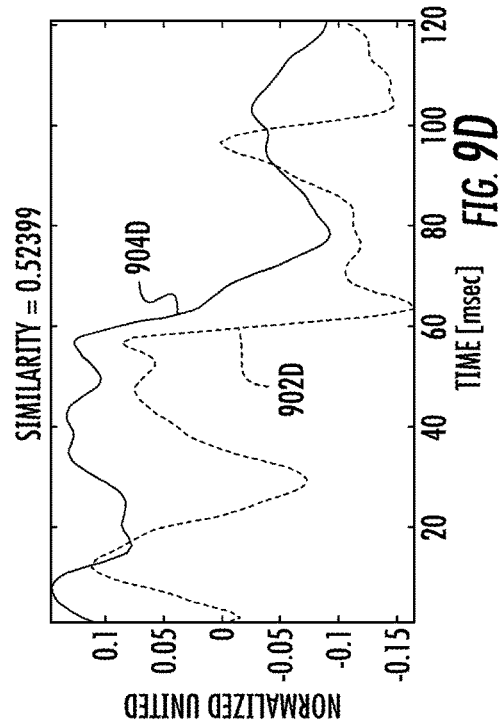
Figure 9C:
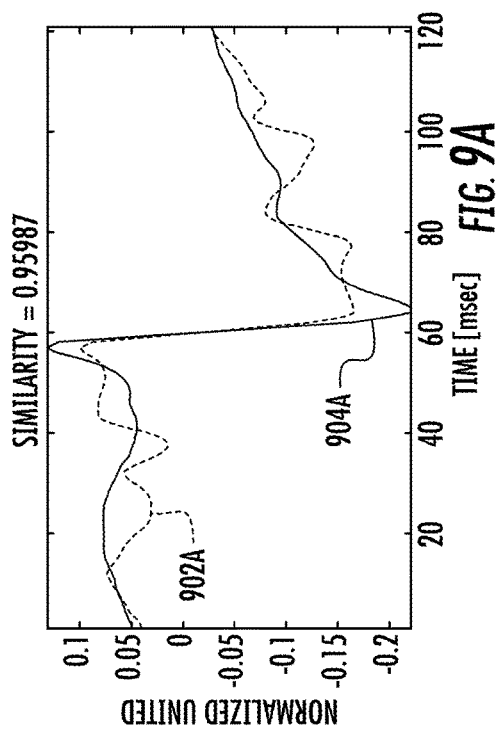
Figure 9D:
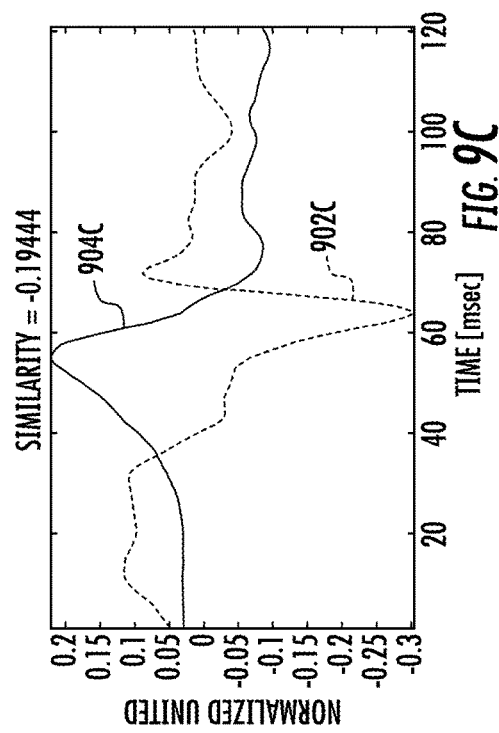

FIGS. 9A through 9D are diagrams illustrating examples of waves 902 and 904 having different degrees of similarity. As shown in FIGS. 9A through 9D, the waves have similarity degrees of 0.95987, 0.25502, 0.19444 and 0.52399, respectively. The atrial activity in FIG. 9A and FIG. 9C is filtered due to low similarity. The atrial activity in FIG. 9A and FIG. 9C are valid RAPs because the cosine similarity index is above 0.5.

In some embodiments, RAPs may be detected by utilizing potential patterns exhibited by RAPs, such as cyclic patterns. Any closed loop in 3D space may potentially represent a cyclic pattern of a RAP. A minimum head to toe distance (i.e., distance between head electrode and toe electrode) may be calculated based on the electrodes participating in the RAP.

For example, the distances between pairs of electrodes (e.g., distances separating any number of electrodes in the wave) in the RAP is calculated. The minimal distance serves as the head to toe. For a RAP defined by the following electrodes (A1, A2, A3, B2, B3, C2, C3, B4, A3), the distances are calculated for A1 to C3, A1 to B4 A1 to A3, A2 to B4, A2 to A3, A3 to A3. Because the Euclidian distance between A3 to itself is 0, the head to toe distance is zero. The head to toe distance serves as a filter for RAPs (i.e. a RAP is valid if the head to toe distance is less than a predetermined threshold distance (e.g., 25 mm)).

The following parameters are extracted for the RAP analysis per recording:
1) Static RAP wave—Represented by electrodes participating in the wave. (e.g. A1, A2, A3, B3, C3 is a wave that start at electrode A1 and terminate at electrode C3). RAP indicators include forming a resemblance of a circle and consecutive electrodes close together.
2) Number of cycles in RAP—Calculate the minimum of two measurements: (1) The duration of RAP divided by the average CL; and (2) the number of actual complex waves forming the RAP. The larger the number of cycles, then indicator of a higher likelihood of pansystolic activation.
3) % CL—The average percentage of cycle length of all complex waves participated in the RAP. If more than 50%, then indicator of a higher likelihood of pansystolic activation.
4) Start—end of RAP: The start and time points of the RAP. From the first time annotation of the first complex wave in the RAP to the last time annotation of the last complex wave participated in the RAP.
5) Wave Duration=(End−Start) in seconds
6) Head to Toe (mm)—Euclidian distance in millimeters between the first electrode to the last electrode of the static wave. Smaller distances are factors indicating higher likelihood of a RAP.
7) Head to Toe (msec)=average cycle length during RAP—average duration of complex waves forming the RAP. Smaller ACLs are factors indicating higher likelihood of a RAP.
8) # of S-waves (% S-wave)—is the number (or percentage) of S-waves in the complex waves participating in the RAP. Higher % is factor indicating higher likelihood of a RAP and may imply that a focal source is adjacent to the RAP.
9) First S-wave—does the first electrode of the static RAP starts with S-wave at least one time? If yes, then factor indicating higher likelihood of a RAP and also may imply that a focal source is adjacent to the RAP and may imply that a focal source is adjacent to a RAP.

FIGS. 10A and 10B are illustrations of an exemplary static representation of a RAP corresponding to the first row of data in Table 1002 in FIG. 10E. FIG. 10A is an illustration of an exemplary wave 1004 propagating through 3 dimensional (3D) space between electrodes. FIG. 10B illustrates electrograms of relevant electrodes shown in FIG. 10A.

FIGS. 10C and 10D are illustrations of an exemplary RAP from simulated data. FIG. 10C is an illustration of an exemplary wave 1006 propagating through 3 dimensional (3D) space between electrodes. FIG. 10D illustrates electrograms of relevant electrodes shown in shown in FIG. 10C. The atrial annotations of FIG. 10C includes 13 evenly spaced annotations during a cycle length of 180 msec, starting at electrode A1 and ending at B2. FIG. 10C represents a pansystolic activation spanning 100% of the cycle, with annotation along six cycles with a phase shift of 30 msec.

After the complex waves are filtered and unified, a RAP is determined as a potential ablation ROI. For example, at least 2 consecutive "same" pansystolic activations may be regarded as a RAP. Activations may be regarded as the same waves when a percentage (or number) of identical electrode transitions between the waves is equal to or greater than a transition percentage threshold (e.g., 35%).

As described above, in some embodiments, different RAP detection algorithms may each provide RAP score information (e.g., a value) which indicate a likelihood or probability that a potential RAP source is detected using the algorithm. For example, score information may be based on a similarity between two or more atrial activations over different cycles. Score information may be based on the comparison of identified centers of two or more pansystolic activations. Score information may be based on a RAP intensity value of an ECG signal over an interval of time may be calculated as:

$$\text{RAP Intensity} = \text{SUM}(\text{Event}(n)^* \text{\# of turns @event}) \quad \text{Equation 2}$$

The method 600 ends upon the detection of a RAP activation source.

Outer Circle To Inner Circle Activation Spreads

As described above, RAP detection may also include identification of outer circle to inner circle activation spreads using circular type (e.g., Lasso, PentaRay) catheters. For example, a catheter comprising a number of non-overlapping concentric loops and having poles arranged in rows separated by 90 degrees can be used to detect the IC ECG signals and LATs for each signal, such as a catheter described in the application JNJ-BIO5643USNP4 titled "Non-Overlapping Loop-Type Or Spline-Type Catheter To Determine Activation Source Direction And Activation Source Type, which is being filed simultaneous with the present application and is incorporated by reference as if fully set forth.

Figure 11:
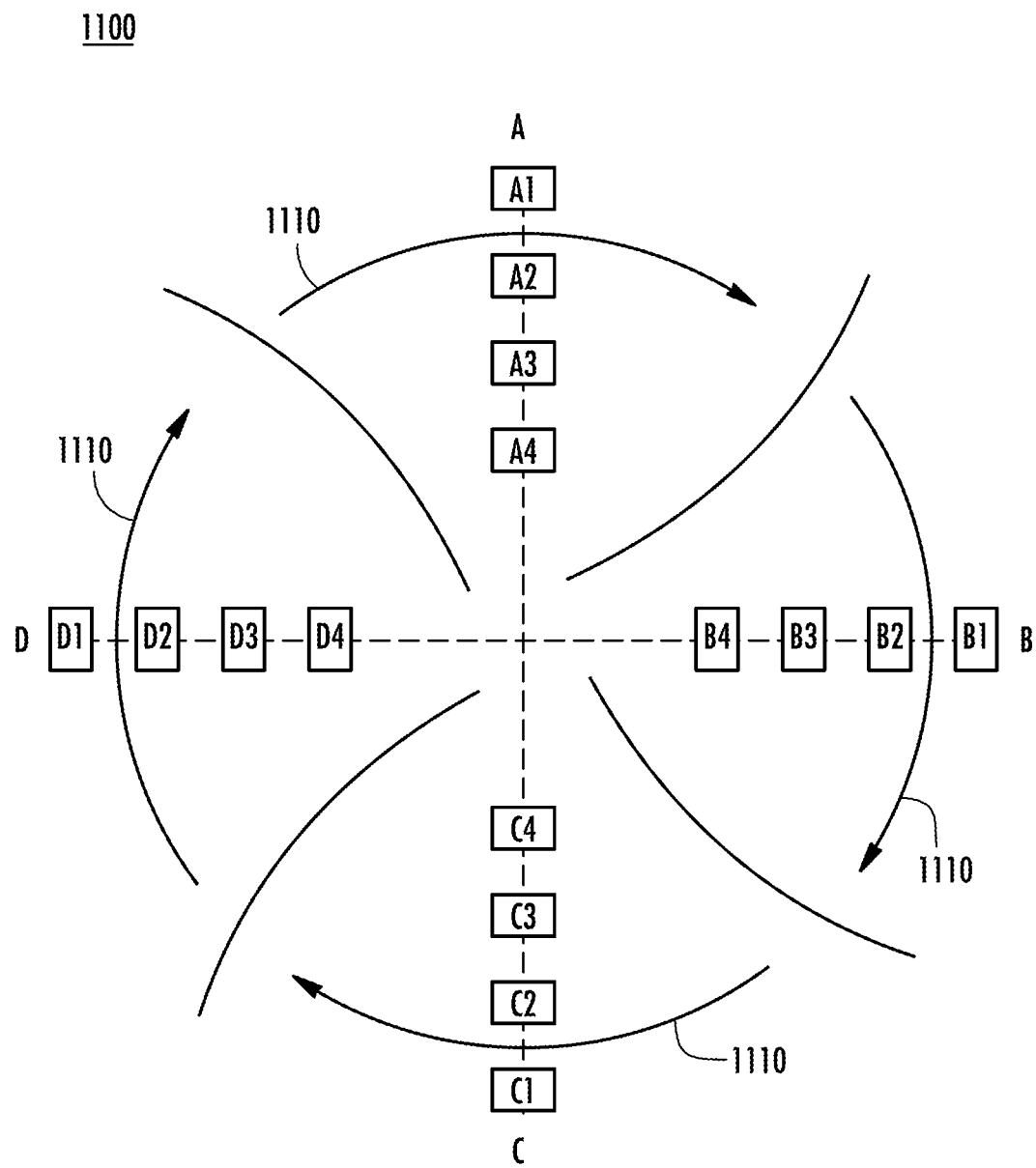
FIG. 11 is a diagram of an example electrode configuration for identifying a wave front direction of activation to determine the origin of activation for a rotational activation pattern.

FIG. 11 is a diagram of an example electrode configuration 1100 that may be used to identify a wave front direction of activation to determine the origin of activation for a rotational activation pattern. In this example, the activation sequence of electrodes may occur in a circular or rotational pattern. For example, as a wave front 1110 approaches the catheter, electrodes A1, A2, A3, and A4 detect the wave front 1110 and activate substantially simultaneously. The activation of electrodes A1, A2, A3, and A4 are recorded in the system as recorded signals. As the wave front 1110 continues its path, electrodes B1, B2, B3, and B4 detect the wave front 1110 and activate substantially simultaneously. The activation of electrodes B1, B2, B3, and B4 are recorded in the system as recorded signals. The activation of electrodes B1, B2, B3, and B4 are recorded in the system as recorded signals. Following the activation of electrodes B1, B2, B3, and B4, electrodes C1, C2, C3, and C4 detect the wave front 1110 and activate substantially simultaneously. The activation of electrodes C1, C2, C3, and C4 are recorded in the system as recorded signals. Following the activation of electrodes C1, C2, C3, and C4, electrodes D1, D2, D3, and D4 detect the wave front 1110 and activate substantially simultaneously. The activation of electrodes D1, D2, D3, and D4 are recorded in the system as recorded signals. In this example, a rotational pattern of the outer circle may cover most of the cycle length (CL). As the catheter is moved toward the center of the rotational activity, a shortening of the rotational pattern may be observed.

Figure 12:
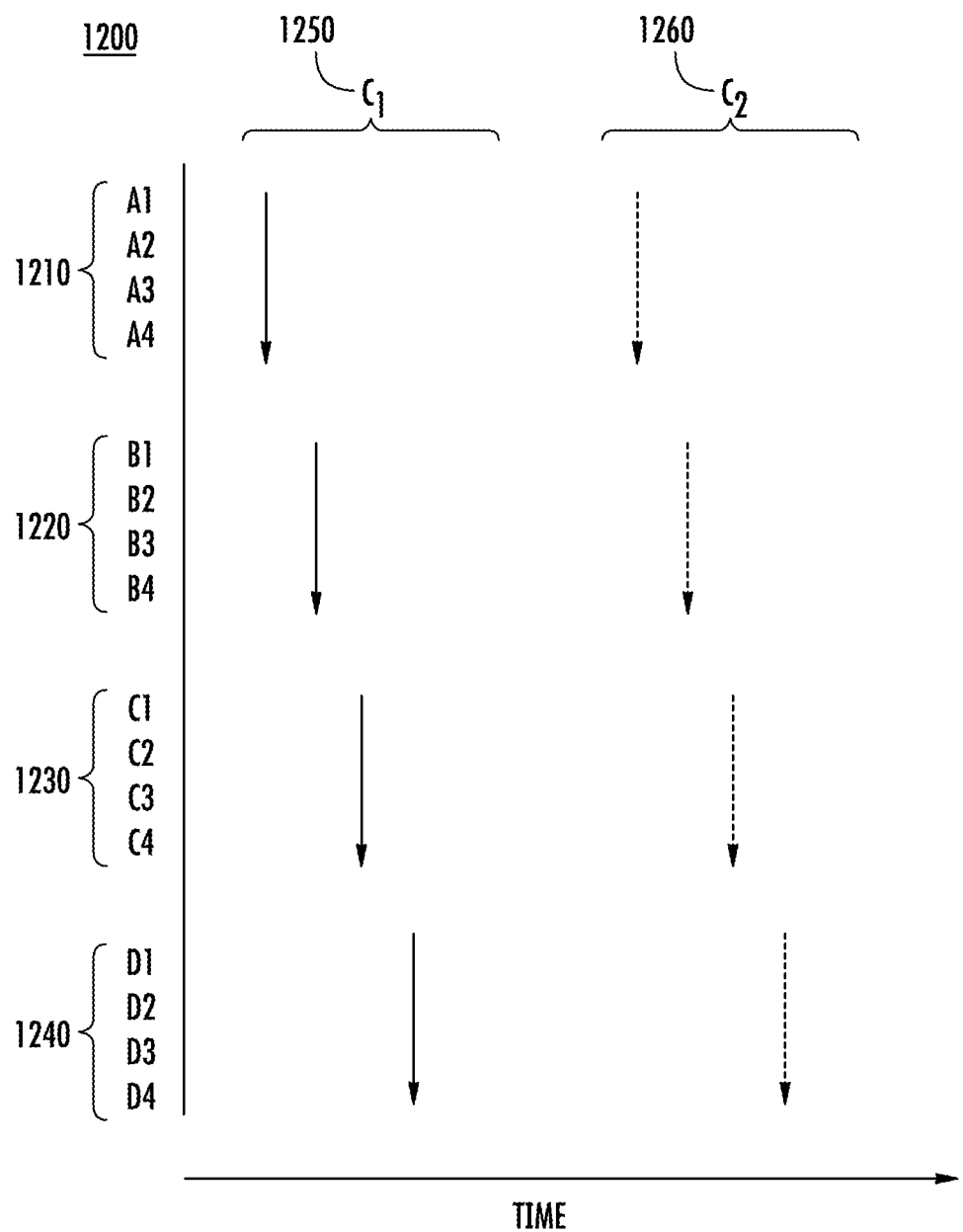
FIG. 12 is a diagram of an example of recorded signals from a catheter based on the electrode activation times for a rotational activation pattern.

FIG. 12 is a diagram of an example of recorded signals 1200 from a catheter with an electrode configuration of FIG. 11. The recorded signals 1200 from the catheter in this example are based on the electrode activation times for a rotational activation pattern and may be displayed on a display. In this example, electrode set A 1210 comprises electrodes A1, A2, A3, and A4. Electrode set B 1220 comprises electrodes B1, B2, B3, and B4. Electrode set C 1230 comprises electrodes C1, C2, C3, and C4. Electrode set D 1240 comprises electrodes D1, D2, D3, and D4. Although an unlimited number of cycles may be shown, in this example, two cycles of rotational activity are shown as $C_1$ 1250 and $C_2$ 1260 for simplicity. In the first cycle $C_1$ 1250, the wave front 1110 substantially simultaneously activates all the electrodes in electrode set A 1210 and the activation of the electrodes in electrode set A 1210 is recorded in the system as recorded signals. As the wavefront 1110 moves along its rotational path, it substantially simultaneously activates all the electrodes in electrode set B 1220 and the activation of the electrodes in electrode set B 1220 is recorded in the system as recorded signals. The wave front 1110 then continues along its rotational path and substantially simultaneously activates all the electrodes in electrode set C 1230 before then finally substantially simultaneously activating electrode set D 1240. The activation of the electrodes in electrode set C 1230 and electrode set D 1240 are respectively recorded in the system as recorded signals. This activation cycle then repeats in $C_2$ 1260. Based on this information and the arrangement of recorded signals 1200, the system may determine that wave front 1110 is a rotational activation pattern and that the catheter is at the origin of activation.

Figure 13:
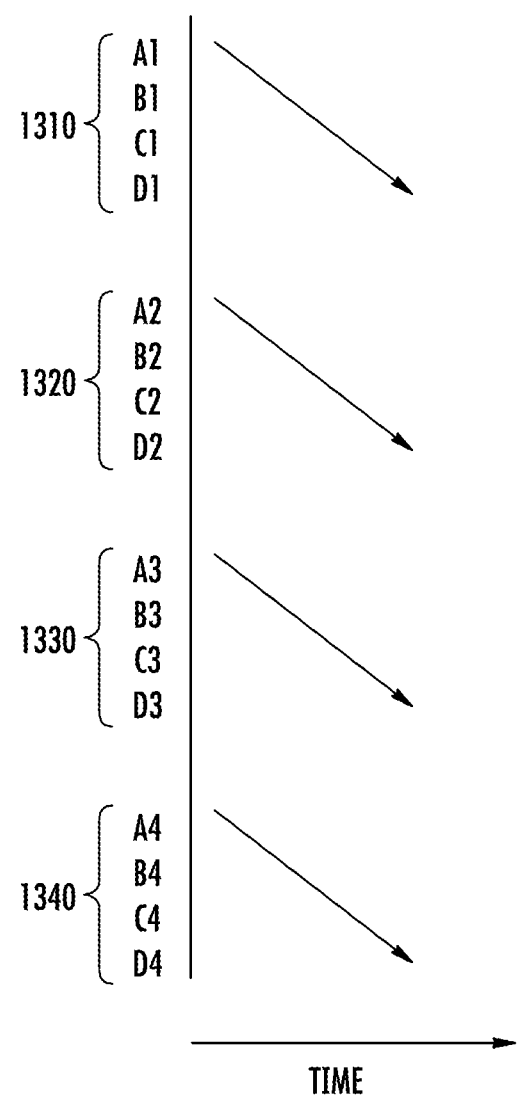
FIG. 13 is a diagram of another example of recorded signals from a catheter based on the electrode activation times for a rotational activation pattern.

FIG. 13 is a diagram of another example of recorded signals 1300 from a catheter with an electrode configuration of FIG. 11. The recorded signals 1300 from the catheter in this example are based on the electrode activation times for a rotational activation pattern and may be displayed on a display. In this example, the same data of FIG. 12 is displayed in an alternate configuration. In this example, the recorded signals 1300 may be arranged according to a predefined template or configuration that may be manually changed by the user or automatically updated by using an algorithm to display the optimal configuration based on the sequence of activation along each of the electrodes' rows.

Referring to FIG. 13, electrode set 1 1310 comprises electrodes A1, B1, C1, and D1. Electrode set 2 1320 comprises electrodes A2, B2, C2, and D2. Electrode set 3 1330 comprises electrodes A3, B3, C3, and D3. Electrode set 4 1340 comprises electrodes A4, B4, C4, and D4. In this example the wave front 1110 substantially simultaneously activates electrodes A1, A2, A3, and A4 and the activation of these electrodes is recorded in the system as recorded signals. As the wavefront 1110 moves along its rotational path, it substantially simultaneously activates electrodes B1, B2, B3, and B4 and the activation of these electrodes is recorded in the system as recorded signals. The wave front 1110 then continues along its rotational path and substantially simultaneously activates electrodes C1, C2, C3, and C4 before then finally substantially simultaneously activating electrodes D1, D2, D3, and D4. The activation of electrodes C1, C2, C3, and C4, and electrodes D1, D2, D3, and D4 are respectively recorded in the system as recorded signals.

As described above, the score information for one or more algorithms (e.g., Activation Based Algorithm and Outer Circle To Inner Circle Activation Spread algorithm) may be provided and used to determine a potential ablation ROI.

It should be understood that many variations are possible based on the disclosure herein. Although features and elements are described above in particular combinations, each feature or element can be used alone without the other features and elements or in various combinations with or without other features and elements.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements methods described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method comprising:
  acquiring, via a plurality of sensors, electro-cardiogram (ECG) signals over time, each ECG signal acquired via one of the plurality of sensors and representing electrical activity of one of a plurality of different areas the heart;
  determining, for each of the plurality of sensors, one or more local activation times (LATs) each indicating a time of activation of a corresponding ECG signal;
  constructing, for each sensor having a corresponding LAT in a window of time, a simple wave propagating between the sensor and one or two neighboring sensors in which the corresponding ECG signal comprises an LAT in the window of time determined to have valid conduction velocity;
  constructing, in the window of time, complex waves from overlapping simple waves; and detecting one or more atrial rotational activity pattern (RAP) source areas of activation in the heart based on the complex waves, wherein one or more maps are displayed for visually indicating the one or more RAP source areas of activation in the heart.

2. The method of claim 1, further comprising:

generating, based on the detected one or more RAP source areas of activation, mapping information of the detected one or more RAP source areas of activation in the heart; and providing the mapping information for the one or more maps representing at least one of the electrical activity of the heart and the spatio-temporal manifestation of the electrical activity of the heart.

3. The method of claim 2, further comprising providing RAP score information indicating a likelihood of the detection of the one or more RAP source areas of activation.

4. The method of claim 1, wherein detecting whether one or more RAP source areas of activation in the heart is indicated further comprises:

selecting a length of the window of time of the LATs, to be equal to an average cycle length of the ECG signals.

5. The method of claim 1, further comprising filtering and unifying the complex waves.

6. The method of claim 1, wherein detecting one or more RAP source areas of activation in the heart further comprises:

detecting the one or more RAP source areas from two or more consecutive pansystolic waves which span equal to or greater than a predetermined percentage of a cycle length (CL) that is based on a plurality of activation cycles.

7. The method of claim 1, wherein detecting one or more RAP source areas of activation in the heart further comprises identifying outer circle to inner circle activation spreads using a circular type catheter.

8. A system comprising:

a plurality of sensors configured to acquire a plurality of electro-cardiogram (ECG) signals each representing electrical activity of one of a plurality of different areas of a heart over time;

a processing device comprising one or more processors configured to:

determine, for each of the plurality of sensors, one or more local activation times (LATs) each indicating a time of activation of a corresponding ECG signal;

construct, for each sensor having a corresponding LAT in a window of time, a simple wave propagating between the sensor and one or two neighboring sensors in which the corresponding ECG signal comprises an LAT in the window of time determined to have valid conduction velocity;

construct, in the window of time, complex waves from overlapping simple waves; and detect whether one or more atrial rotational activity pattern (RAP) source areas of activation in the heart based on the complex waves, wherein one or more maps are displayed for visually indicating the one or more RAP source areas of activation in the heart.

9. The system of claim 8, wherein the one or more processors is further configured to:

generate, based on the detected one or more RAP source areas of activation, mapping information of the detected one or more RAP source areas of activation in the heart; and provide the mapping information for the one or more maps representing at least one of the electrical activity of the heart and the spatio-temporal manifestation of the electrical activity of the heart.

10. The system of claim 9, wherein the one or more processors is further configured to provide RAP score information indicating a likelihood of the detection of the one or more RAP source areas of activation.

11. The system of claim 8, wherein detecting whether one or more RAP source areas of activation in the heart is indicated further comprises:

selecting a length of the window of time of the LATS, to be equal to an average cycle length of the ECG signals.

12. The system of claim 8, wherein the one or more processors is further configured to filter and unify the complex waves.

13. The system of claim 8, wherein detecting one or more RAP source areas of activation in the heart further comprises:

detecting the one or more RAP source areas from two or more consecutive pansystolic waves which span equal to or greater than a predetermined percentage of a cycle length (CL) that is based on a plurality of activation cycles.

14. The system of claim 8, wherein detecting one or more RAP source areas of activation in the heart further comprises identifying outer circle to inner circle activation spreads using a circular type catheter.

15. A non-transitory computer readable medium comprising instructions for causing a computer to execute a method comprising:

detecting, via a plurality of sensors, electro-cardiogram (ECG) signals over time, each ECG signal detected via one of the plurality of sensors and indicating electrical activity of a heart;

acquiring, via a plurality of sensors, electro-cardiogram (ECG) signals over time, each ECG signal acquired via one of the plurality of sensors and representing electrical activity of one of a plurality of different areas the heart;

determining, for each of the plurality of sensors, one or more local activation times (LATs) each indicating a time of activation of a corresponding ECG signal;

constructing, for each sensor having a corresponding LAT in a window of time, a simple wave propagating between the sensor and one or two neighboring sensors in which the corresponding ECG signal comprises an LAT in the window of time determined to have valid conduction velocity;

constructing, in the window of time, complex waves from overlapping simple waves; and detecting one or more atrial rotational activity pattern (RAP) source areas of activation in the heart based on the complex waves, wherein one or more maps are displayed for visually indicating the one or more RAP source areas of activation in the heart.

16. The computer readable medium of claim 15, wherein the instructions further comprise:

generating, based on the detected one or more RAP source areas of activation, mapping information of the detected one or more RAP source areas of activation in the heart; and providing the mapping information for the one or more maps representing at least one of the electrical activity of the heart and the spatio-temporal manifestation of the electrical activity of the heart.

17. The computer readable medium of claim 15, wherein detecting whether one or more RAP source areas of activation in the heart is indicated further comprises:
  selecting a length of the window of time of the LATs, to be equal to an average cycle length of the ECG signals.

18. The computer readable medium of claim 15, wherein detecting one or more RAP source areas of activation in the heart is further comprises identifying outer circle to inner circle activation spreads using a circular type catheter.

* * * * *

UNITED STATES PATENT AND TRADEMARK OFFICE
CERTIFICATE OF CORRECTION

| | | |
|---|---|---|
| PATENT NO. | : 10,582,894 B2 | |
| APPLICATION NO. | : 15/404225 | |
| DATED | : March 10, 2020 | |
| INVENTOR(S) | : Yaniv Ben Zrihem et al. | |

It is certified that error appears in the above-identified patent and that said Letters Patent is hereby corrected as shown below:

On the Title Page
Item (72), under "Inventors", in Column 1, Line 2, delete "Zemmer (IL);" and insert -- Zemer (IL); --, therefor.
Item (72), under "Inventors", in Column 1, Line 5, delete "Tivon (IL);" and insert -- Tiv'on (IL); --, therefor.
Item (72), under "Inventors", in Column 1, Line 7, delete "Tzorit (IL)" and insert -- Tzurit (IL) --, therefor.

In the Specification
In Column 2, Line 51, delete "ROIs; and" and insert -- ROIs; --, therefor.
In Column 2, Line 64, delete "exemplary" and insert -- of exemplary --, therefor.
In Column 3, Line 37, delete "interest" and insert -- interests --, therefor.
In Column 6, Line 23, delete "3A," and insert -- 3A. --, therefor.
In Column 9, Line 2, delete "increase" and insert -- increased --, therefor.
In Column 13, Line 16, delete "Al to B4" and insert -- Al to B4, --, therefor.
In Column 13, Line 43, delete "seconds" and insert -- seconds. --, therefor.
In Column 14, Line 44, delete "Type," and insert -- Type", --, therefor.

In the Claims
In Column 16, Line 55, in Claim 1, delete "the" and insert -- of the --, therefor.
In Column 17, Line 56, in Claim 8, delete "detect whether" and insert -- detect --, therefor.
In Column 18, Line 12, in Claim 11, delete "LATS," and insert -- LATs, --, therefor.
In Column 18, Line 39, in Claim 15, delete "the" and insert -- of the --, therefor.

Signed and Sealed this
Thirty-first Day of January, 2023

*Katherine Kelly Vidal*

Katherine Kelly Vidal
*Director of the United States Patent and Trademark Office*